United States Patent [19]
Bieniarz et al.

[11] Patent Number: 5,582,984
[45] Date of Patent: Dec. 10, 1996

[54] METHODS OF USE OF PHENANTHRIDIUM DNA INTERCALATORS FOR FLUORESCENCE DETECTION

[75] Inventors: Christopher Bieniarz, Highland Park; Jeffrey B. Huff, Park Ridge; Denis R. Henrard, Lake Forest, all of Ill.

[73] Assignee: Abbott Laboratories, Abbott Park, Ill.

[21] Appl. No.: 268,043

[22] Filed: Jun. 29, 1994

Related U.S. Application Data

[62] Division of Ser. No. 86,285, Jun. 30, 1993, abandoned.

[51] Int. Cl.$^6$ .................................................. C12Q 1/68
[52] U.S. Cl. ........................... 435/6; 536/25.4; 546/109
[58] Field of Search ................... 435/6, 91.2; 536/25.4; 546/109

[56] References Cited

U.S. PATENT DOCUMENTS 4,683,195   7/1987   Mullis et al. .................................. 435/6

OTHER PUBLICATIONS

Neidle, Basic Life Sci., 38(Mechanisms DNA Damage Repair), pp. 257–264, Ed. by Simic et al., Pienum Pres, N.Y. 1986.

Roques et al., C. R. Hebd. Séances Acad. Sci., Ser. D, 283(11), 1365–7, 1976.

*Primary Examiner*—W. Gary Jones
*Assistant Examiner*—Scott W. Houtteman
*Attorney, Agent, or Firm*—David L. Weinstein

[57] ABSTRACT

Phenanthridium compounds are provided which are comprised of intercalators and substituted intercalator segments having a functionalized chain or chains which provide a high affinity for binding to the DNA molecule and show reduced self-quenching, while providing superior transport kinetics. The compounds have been found to provide enhanced fluorescence when bound to a DNA molecule within a fluorescent flow cytometry environment which is about eight to ten times brighter in fluorescence than "bis" structure intercalators and other known intercalators utilized in flow cytometry environment, said enhancement of fluorescence allows a drastic reduction in the amount of intercalator needed for applications of similar sensitivity than those using known intercalators. Substantial improvements in material use efficiency, accuracy and dependability of various DNA studies are direct results of the inventive intercalator compounds, said compounds having use in known DNA intercalator applications inclusive of flow cytometry, gel electrophoresis, DNA detection, immunoassay for DNA, fluorescence in situ hybridization assays, DNA sequencing application, therapeutic application and conversion staining methodologies.

7 Claims, 14 Drawing Sheets

METHODS OF USE OF PHENANTHRIDIUM DNA INTERCALATORS FOR FLUORESCENCE DETECTION

This is a divisional application of application Ser. No. 08/086,285, filed on Jun. 30, 1993, now abandoned.

BACKGROUND OF THE INVENTION

The present invention relates to a compound comprised of an intercalator or substituted intercalator segment derivatized with functionalized chains having high affinity for binding to a DNA molecule. More particularly, the invention relates to use of these intercalator compounds which exhibit improved binding to a DNA molecule within known methodologies requiring intercalator insertion into the DNA molecule. Still, the invention relates to enhanced binding of DNA molecules by an intercalator functioning segment utilized in labeling, capture, therapeutic insertion, assay and the like, with improved performance of the intercalator due to the increased utilization efficiency of the compounds.

The term "intercalator" was introduced into the chemistry field over 30 years ago to describe the insertion of planar aromatic or heteroaromatic compounds between adjacent base pairs of double stranded DNA (dsDNA). Many DNA intercalating compounds elicit biologically interesting properties. It is generally agreed that these properties are related to their reactivity with DNA. In the search for more active compounds, it is logical to design molecules with the highest possible affinity for DNA. In 1990, it was reported that complexes of ethidium homodimer with dsDNA performed at ratios of one dimer per four to five base pairs, and were stable to electrophoresis on agarose gels. This allowed fluorescence, detection and quantitation of DNA fragments with picogram sensitivity after separation and complete absence of background stain. Such a result has been sought through various manipulations of intercalator compounds, for example, by functional compounds made up of DNA intercalating dyes. As a result of these efforts, DNA intercalating agents utilizing ethidium bromide have been used in various DNA analytical procedures.

Various reported DNA intercalating agents utilizing ethidium bromide have been used in a multitude of DNA analytical procedures, for example:

Christen, et al., "An Ethidium Bromide-Agarose Plate Assay for the Nonradioactive Detection of CDNA Synthesis", Anal. Biochem., May 1, 1989, 178 (2), pp. 269–272, report ethidium bromide was used to determine the success of cDNA synthesis reactions. Since ethidium bromide in agarose can be used to quantitate RNA and DNA, conditions under which the greater fluorescence of double-stranded DNA is utilized were devised to assay double stranded DNA synthesis from mRNA. Ethidium bromide at 5 micrograms/ml in agarose allowed quantitative detection of cDNA in the range of 0.03 to 0.0015 microgram. Sodium dodecyl sulfate had an adverse effect on the measurement of cDNA. Subsequent cDNA analysis by alkaline gel electrophoresis and staining in 5 micrograms/ml ethidium bromide allowed accurate and rapid sizing of cDNA and required only 0.01–0.05 microgram cDNA.

Petersen, S. E., "Accuracy and Reliability of Flow Cytometry DNA Analysis Using a Simple, One-Step Ethidium Bromide Staining Protocol", Cytometry, July, 1986, 7 (4), pp. 301–306, reports that sources of variation and error were investigated for a simple flow cytometric analysis of DNA content of detergent-isolated nuclei stained with ethidium bromide.

In "Ethidium Bromide in the Detection of Antibodies to DNA and of Circulating DNA by Two-Stage Counterimmunoelectrophoresis", J. Immunol. Methods, Dec. 17, 1985, 85 (1), pp. 217–220, Riboldi, et al., report that in an attempt to overcome the limitations of counterimmunoelectrophoresis in the detection of precipitating anti-DNA antibodies or circulating DNA, ethidium bromide was used to increase the visibility of the precipitating lines and to confirm their specificity.

W. A. Denny reported in "DNA-Intercalating Ligands as Anti-Cancer Drugs: Prospects for Future Design", Anticancer Drug Des., December, 1989, 4 (4), pp. 241–263, that interest in DNA-intercalating ligands as anti-cancer drugs has developed greatly since the clinical success of doxsorubicin.

A number of agents have been described for labeling nucleic acids, whether probe or target, for facilitating detection of target nucleic acid. Suitable labels may provide signals detectable by fluorescence, radioactivity, colorimetry, X-ray diffraction or absorption, magnetism or enzymatic activity, and include, for example, fluorophores, chromophores, radioactive isotopes, enzymes, and ligands having specific binding partners.

Fluorescent dyes are suitable for detecting nucleic acids. For example, ethidium bromide is an intercalating agent that displays increased fluorescence when bound to double stranded DNA rather than when in free solution. Ethidium bromide can be used to detect both single and double stranded nucleic acids, although the affinity of ethidium bromide for single stranded nucleic acid is relatively low. Ethidium bromide is routinely used to detect nucleic acids following gel electrophoresis. Following size fractionation on an approximate gel matrix, for example, agarose or acrylamide, the gel is soaked in a dilute solution of ethidium bromide.

The use of fluorescence labeled polynucleotide probes and polynucleotide hybridization assays have been reported. According to these methods, probes are prepared by attaching a particular absorber-emitter moieties to the three prime and five prime ends of the nucleic acid fragments. The fragments are capable of hybridizing to adjacent positions of a target DNA so that if both fragments are hybridized, the proximity of the absorber and emitter moieties results in the detectable emitter fluorescence. According to these methods, the fluorescent dye is introduced into the target DNA after all in vitro nucleic acid polymerizations have been completed. The inhibitory effects of intercalating agents on nucleic acid polymerases have been described in numerous locations.

DNA binding dyes are useful as antibiotics because of the inhibitory effects of nucleic acid replication processes that result from the agent binding to the template. The use of intercalating agents for blocking infectivity of influenza or herpes viruses have been reported. It has also been reported and described that a number of DNA binding agents, both intercalators and nonintercalators, inhibit nucleic acid replication. For example, ethidium bromide inhibits DNA replication.

Methods have been provided for detecting a target nucleic acid in a sample. These methods comprise the steps of (a) providing an amplified reaction mixture that comprises a sample, a DNA binding agent, where said agent is characterized by providing a detectable signal when bound to double stranded nucleic acid, which signal is distinguishable from the signal provided by said agent when it is unbound, and reagents for amplification; (b) determining the amount of signal produced by the mixture of step (a); (c) treating said mixture under conditions for amplifying the target nucleic acid; (d) determining the amount of said signal produced by the mixture of step (c); and (e) determining if amplification has occurred. These DNA binding intercalating agents, such as ethidium bromide or ethidium homodimer allow fluorometric study of the interaction of various molecules with DNA.

The intercalating agent useful for DNA binding or detecting amplified nucleic acids is an agent or moiety capable of insertion between stacked base pairs in the nucleic acid double helix. Intercalating agents such as ethidium homodimer and ethidium bromide fluoresce more intensely when intercalated into double stranded DNA than when bound to single stranded DNA, RNA, or in solution. Other uses of intercalators have been in the field of separation and isolation or purification of nucleic acids from complex biological or clinical specimens.

Various methods of separating deoxyribonucleic acids (DNA) from liquid biological samples are known in the art, but are very time consuming or otherwise plagued by complication. It is known that DNA adheres to nitrocellulose. The liquid sample containing DNA is applied to a nitrocellulose filter and the DNA adheres or binds to the filter.

Another method of separating DNA from samples is ultracentrifugation with sucrose or cesium chloride density gradients. The DNA is separated from other macromolecules such as proteins by this method according to the buoyant density or sedimentation coefficient. The biological sample is layered onto the density gradient in a centrifuge tube and is spun at very high speeds for long periods of time for DNA to travel through the density gradient. This method, although satisfactory, is very time consuming and labor intensive. The centrifugation time may be 20 hours or more per sample. Furthermore, if the sample is spun too long, the DNA will separate from the sample but will pass entirely through the gradient to the very bottom of the centrifuge tube along with other constituents in the sample. Therefore, this method is also not suitable as a fast and easy method for separating DNA from complex samples.

Agarose polyacrylamide gel electrophoresis is also used to separate DNA from biological samples. In this method, the sample is applied to one end of a glass or plastic receptacle containing the gel and an electric current is applied across the length of the receptacle. The negatively charged nucleic acid molecules move toward the anode, the larger molecules moving more slowly. The rates of migration of the molecules depend on their molecular weights and on the concentration and degree of cross linking in the gel material. The DNA is then removed from the gel by cutting out that portion of the gel in which the DNA is located and finally extracting the DNA. Again, this method is time consuming and labor intensive, and the DNA must still be separated from the gel. When DNA is separated by the electrophoresis gel method or by centrifugation, it is necessary for the DNA to be stained in some manner to be visualized. Typically, ethidium bromide (EtBr) has been used as the staining agent. Ethidium bromide adheres to the DNA by intercalation between the base pairs of the double helix structure of the DNA.

More recently, an ethidium homodimer has been synthesized and introduced with bifunctional intercalators in order to allow fluorometric study including the interaction of such molecules with DNA. It has been determined that the ethidium homodimer (EthD) binds to dsDNA (double stranded DNA) about two (2) orders of magnitude more strongly than ethidium bromide. Complexes of EthD with dsDNA have performed at a ratio of one dimer per 4 to 5 base pairs and were found to be stable to electrophoresis on agarose base. On binding to dsDNA, the fluorescence quantum yield of the dimer increases 40 fold independent of nucleotide sequence.

Stable dsDNA-fluoropore complexes can be formed to obtain anywhere from several to several thousand fluoropores each, as desired. Under suitable controlled conditions these complexes do not transfer dye to other nucleic acids or proteins. An important property of these complexes is that their fluorescence emission intensity is a linear function of the number of intercalated dye molecules. As high sensitivity fluorescence detection apparatus becomes more generally available, the ability to use dyes to replace, for example, radioactivity for sensitivity detection of DNA, is becoming more and more valuable.

Dye dsDNA complexes represent a novel family of fluorescence labels with a wide range of spectroscopic properties whose composition, structure and size can be tailored to particular applications. DNA molecules can be readily derivated to attach biotin, digoxigenin or any number of other substituents that can be recognized by avidin or antibodies. Such derivatize DNA molecules loaded with dye may allow detection at much higher sensitivity in numerous applications, for example, immunoassay, fluorescence, and in situ hybridization of chromosomes and the like that currently use other fluorescence labels.

Probes with a double stranded region, which provide intercalation sites and a single stranded region to allow recognition by hybridization of specific target sequences, offer another approach to the generation of versatile fluorescent labels. Development of conditions that allow clear discrimination between the binding of intercalators to single and double stranded nucleic acids is an essential prerequisite to the use of such probes.

Fluorescent probes are valuable reagents for the analysis and separation of molecules and cells. Some specific examples of their application are identification and separation from a subpopulation of cells in a mixture of cells by the techniques of fluorescence, flow cytometry, fluorescence-activated cell sorting, and fluorescence microscopy. Other applications include determination of a concentration of a substance or member of a specific binding pair that binds to a second species, or member of the specific binding pair, e.g., antigen-antibody reactions in an immunofluorescent assay. Still another application is the localization of substance in gels and other insoluble supports by the techniques of fluorescence staining.

Choice of fluorescers for these purposes is hampered by various constraints; one being the absorption and emission characteristics of the fluorescer since many ligands, receptors and other binding pair members, as well as other extraneous materials associated with the sample, for example, blood, urine and cerebrospinal fluid, will autofluoresce and interfere with an accurate determination or quantification of the fluorescent signal generated by the fluorescent label when the sample is exposed to the appropriate stimulus. Another consideration is the quantum efficiency of the fluorescer. Yet another concern is self-quenching; this can occur when the fluorescent molecules interact with each other when in close proximity. An additional concern is the non-specific binding of the fluorescer to other compounds or even with the test container.

It has been shown that double stranded DNA (dsDNA) forms spectrophotometric, highly fluorescent complexes with the bis-intercalator ethidium homodimer (EthD). Observations regarding the bis-intercalator EthD suggest that the intercalator can be exploited to generate a family of highly fluorescent stable dsDNA-dye complexes with distinctive properties. Such complexes could be exploited by multiplex detection of dsDNA fragments, as well as many analytical applications in which appropriately diversified dsDNA fragments labeled noncovalently with different dyes could be used as a unique family of fluorescent probes:

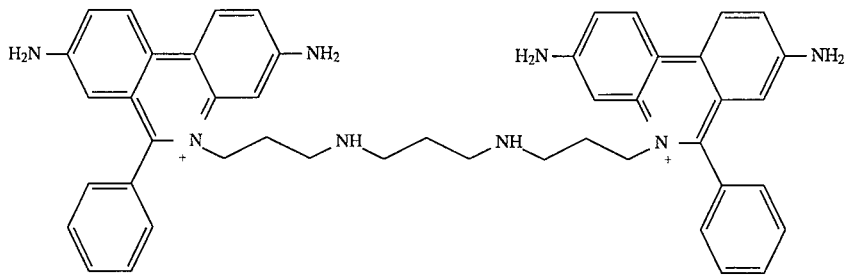

However, this compound may have a tendency to self-quench when bound to DNA. The "bis" structures inhibit each other because the "bis" intercalators cannot simultaneously intercalate.

In flow cytometry apparatuses, cells or other particles are caused to flow in a liquid flow stream so as to facilitate the investigation of certain characteristics thereof. In general, a flow cytometry apparatus is useful for identifying the presence of certain cells or particles of interest, enumerating those cells or particles and, in some instances, providing a sorting capability so as to be able to collect those cells or particles of interest. In a typical flow cytometry apparatus, a fluid sample containing cells is directed through the apparatus in a rapidly moving liquid stream so that each cell passes serially, and substantially one at a time, through a sensing region. Cell volume may be determined by changes in electrical impedance as each cell passes through the sensing region. Similarly, if an incident beam of light is directed at the sensing region, the passing cells scatter such light as they pass therethrough. This scattered light has served as a function of cell shape and size, index of refraction, opacity, granularity, roughness and the like. Further, fluorescence emitted by labeled cells, or autofluorescent cells, which have been excited as a result of passing through the excitation energy of the incident light beam is detectable for identification of cells having fluorescent properties. After cell analysis is performed by the flow cytometry apparatus, those cells that have been identified as having the desired properties may be sorted if the apparatus has been designed with such capability.

Instruments such as flow cytometry apparatuses are particularly useful for researchers and investigators studying various responses, reactions and functions of the immune system. Immunofluorescence studies, as well as fluorescence immunoassays, assist the investigator in identifying and targeting select cells of interest so that disease states, conditions and the like may be properly characterized. In addition to immune system investigations, fluorescence analysis is also quite beneficial in cell biology and morphology investigations, including the study of the substrate of cellular material.

In relying upon fluorescence to provide data and information about cells, the mechanics of performing tests for the fluorescence response is a major consideration in the design of the instrument as well as the results obtained. Specifically, the fluorescent markers, whether such markers be fluorescent stains or dyes, are typically excited by light energy. Usually there is an optimal wavelength which provides the greatest level of excitation for the fluorochromatic marker being used. Once excited, fluorescence emission occurs typically at wavelengths different from the wavelength of excitation. Fluorescence analysis instruments, whether fluorescence microscopes, image analyzers or flow cytometers, are generally designed to detect the fluorescence emission at the wavelength of emission maxima where the fluorescence signal is strongest.

Before the discovery and publication of the utilities of ethidium homodimer as an important intercalator, the usual intercalator of choice was ethidium bromide. Uses of the ethidium bromide intercalators include fluorometric methodologies, quantitative fluorescences of DNA intercalated ethidium bromide on agarose gels, ethidium bromide-agarose plate assay or detection of false DNA analysis and the like. Ethidium bromide and propidium bromide were further used in flow cytometry, as well as applications for direct electronic imaging, direct and rapid quantitation of fluorescence and electrophoretic gels in application as ethidium bromidestain DNA. Ethidium bromide has also been used to increase the visibility of the precipitant lines and to confirm the specificity in two stage counter immunoelectrophoresis methodologies for detection of participating anti-DNA antibodies or circulating DNA. Utilization of ethidium bromide as an intercalator in numerous environments, as well as the more recent utilization of the ethidium homodimer intercalator are well documented in the literature and present the leading edge of intercalator methodology and efficiency.

In a somewhat different application of ethidium bromide as a staining agent, ethidium bromide has been linked to a solid support. U.S. Pat. No. 4,119,521, issued to Chirikjian on Oct. 10, 1978, discloses a fluorescent DNA intercalating agent derivative of activated polysaccharides. The derivatives in the patent function as fluorescent stains to provide direct visualization of the DNA and their fractions, under the excitation of shortwave, ultraviolet radiation. The intercalating agents used in the patent are ethidium halides, with the preferred agent being ethidium bromide. This agent is coupled covalently to an activated polysaccharide such as agarose.

Utilization of ethidium bromide as an intercalator for use in numerous environments, as well as the more recent utilization of the ethidium homodimer intercalator are well documented in the literature and present the leading edge of intercalator methodology and efficiency. However, there remains an ever present need to improve utilization of the intercalators and viability of the use of intercalators with DNA, specifically addressing (1) high affinity for binding the intercalators to the DNA molecule; (2) reduction of self-quenching; and (3) providing superior transport kinetics. Intercalators possessing these qualities reduce the amount of intercalator required for performing one of the many functions involved in the aforementioned methodologies which can also enhance methodologies. In addition, improvement in accuracy and reliability of the various uses of interest is of continuing concern.

SUMMARY OF THE INVENTION

The invention provides compounds comprised of intercalators and substituted intercalator segments having a functionalized chain or chains which provide a high affinity for binding to the DNA molecule and show reduced self-quenching, while providing superior transport kinetics. The inventive intercalators have been found to provide enhanced fluorescence when bound to a DNA molecule within a fluorescent flow cytometry environment which is about eight to ten times brighter in fluorescence than ethidium homodimer utilized in the same flow cytometry environment. This enhancement of fluorescence allows a drastic reduction in the amount of intercalator needed for applications of similar sensitivity than those using the ethidium homodimer or even the lesser desired ethidium bromide intercalator. Substantial improvements in material use efficiency, accuracy, and dependability of various DNA studies are direct results of the intercalator compounds according to the invention.

Improvements in flow cytometry, fluorescence in-situ hybridization assays, gel electrophoresis, DNA detection, immunoassay for DNA, and other DNA studies are substantial. Recent scientific applications addressing the use of intercalators with DNA and multiple methods have shown that the ethidium homodimer is about two orders of magnitude brighter than conventional staining methodology, i.e., ethidium bromide. However, the intercalator compounds in accordance with the present invention provide, for example, a dye which exhibits an eight to ten-fold increase in brightness over that of EthD in the same environment, or about a thousandfold improvement over more conventional staining methodologies. With pre-staining and post-electrophoresis detection, the sensitivity level of radioimmunoassay detection of DNA is now attainable with fluorophores. The compound compositions provided by this invention extends the limits of detection by up to tenfold over EthD, thereby providing a potential for new uses in applications of intercalators for the study of DNA analysis, as well as therapeutics and the like.

DETAILED DESCRIPTION OF THE INVENTION

Figure 1:
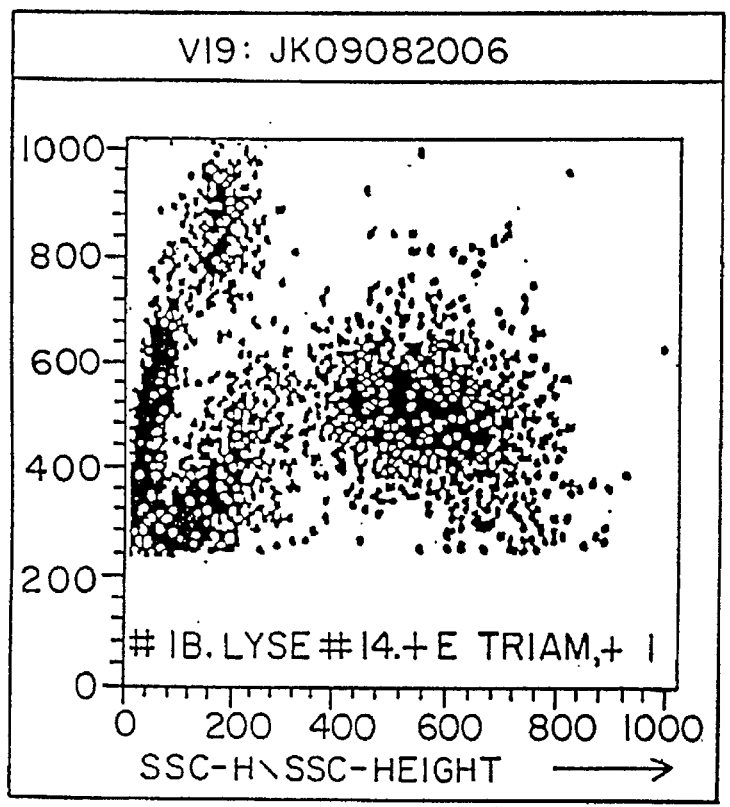
FIG. 1 is a FACScan™ display for side scatter versus forward scatter.

Improved binding to the DNA molecule of intercalators and substituted intercalators is achieved which exhibit high affinity for binding, reduced self-quenching, and superior transport kinetics, especially when compared to ethidium homodimer or other bis-intercalators, by providing intercalator segments with functionalized chains forming compounds having the formula:

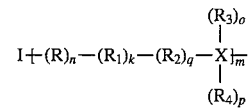

wherein I is an aromatic or heteroaromatic segment; X is a heteroatom or metal ion carrying a positive charge in pH environment of about 4 to about 9; R, $R_1$ and $R_2$ are alkyl, alicyclic, heteroalicyclic, aromatic or heteroaromatic groups; $R_3$ and $R_4$ are hydrogens when X is nitrogen or methyl, ethyl or phenyl groups when X is phosphorus or sulfur; k is zero or an integer from 1 to 10; q is zero or an integer from 1 to 10; m is an integer from 1 to 30; n is an integer from 2 to 20; o is zero or one; and p is zero or one.

A compound comprised of intercalator functionalized with chains containing heteroatoms or metal ions and aliphatic, alicyclic and aromatic segments and combinations thereof having the formula:

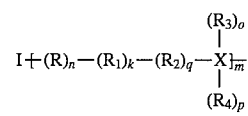

wherein I is an intercalator segment; X is a heteroatom or metal ion; R, $R_1$ and $R_2$ are alkyl, alicyclic, heteroalicyclic, aromatic or heteroaromatic groups; $R_3$ and $R_4$ are hydrogens when X is nitrogen or methyl, ethyl or phenyl groups when X is phosphorus or sulfur; k is zero or an integer from 1 to 10; l is zero or an integer from 1 to 10; m is an integer from 1 to 30; n is an integer from 2 to 20; o is zero or one; and p is zero or one.

A compound comprised of an intercalator functionalized with chains containing heteroatoms and aliphatic, alicyclic, cyclohexyl, aromatic segments or combinations thereof having the formula:

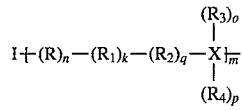

wherein I is an intercalator segment; X is a main group element phosphorus or sulfur yielding, respectively polyphosphonium or polysulfonium moieties; R, $R_1$ and $R_2$ are alkyl, alicyclic, heteroalicyclic, aromatic or heteroaromatic groups; $R_3$ and $R_4$ are hydrogens when X is nitrogen or methyl, ethyl or phenyl groups when X is phosphorus or sulfur; k is zero or an integer from 1 to 10; q is zero or an integer from 1 to 10; m is an integer from 1 to 30; n is an integer from 2 to 20; o is zero or one; and p is zero or one; where X is sulfur, o or p are zero; and where X is phosphorus, o and p are one.

A compound comprised of aromatic or heteroaromatic segments functionalized with positively charged chains having the formula:

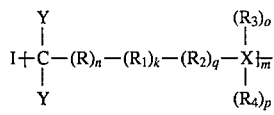

wherein Y is a side chain comprised of positively charged heteroatoms or metal ions in an aliphatic, alicyclic, heteroalicyclic, aromatic or heteroaromatic group or combinations thereof; I is an aromatic or heteroaromatic segment; X is a heteroatom; R, $R_1$ and $R_2$ are alkyl, alicyclic, heteroalicyclic, aromatic or heteroaromatic group; $R_3$ and $R_4$ are hydrogens when X is nitrogen or methyl, ethyl or phenyl groups when X is phosphorus or sulfur; k is zero or an integer from 1 to 10; q is zero or an integer from 1 to 10; m is an integer from 1 to 30; n is an integer from 2 to 20; o is zero or one; p is zero or one; where X is sulfur, o and p are zero; and where X is phosphorus o and p are one.

A compound as above wherein Y has the formula:

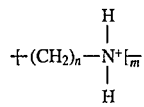

Further, a compound comprised of intercalators functionalized with chains containing metal atoms and alkyl, alicyclic, or aromatic segments or combinations having the formula:

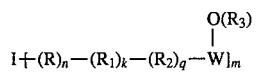

wherein W is aluminum, boron or a Lewis acid metal; I is an intercalator segment; R, $R_1$, $R_2$ and $R_3$ are alkyl, alicyclic, or aromatic groups; k is zero or an integer from 1 to 10; q is zero or an integer from 1 to 10; m is an integer from 1 to 30; and n is an integer from 2 to 20.

An intercalator composition functionalized with positively charged chains where the positive charges are located on an aliphatic, alicyclic, aromatic or the combination thereof with a polyaminic ester group of main chain polyphosphate, polyphosphonate or polysulfate, having the formula:

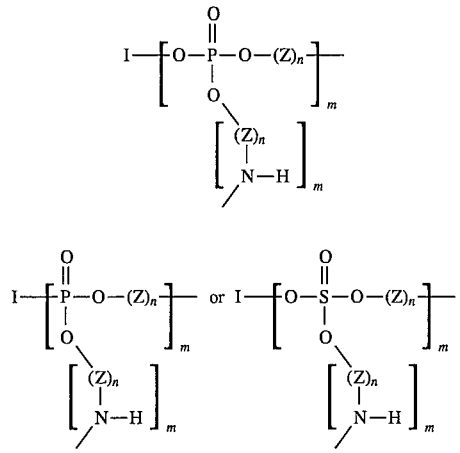

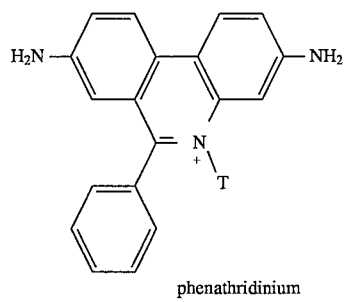

wherein I is an intercalator segment; P is a phosphorus atom; S is a sulfur atom; Z is an aliphatic, alicyclic or aromatic chain or the combination thereof; n is from 2 to 20, preferably 2 or 3; and m is from 1 to 30, preferably, 3–10.

The present intercalator compounds are substantially monointercalators, versus the polyfunctional (bis) intercalators, as represented by the ethidium homodimer. The monointercalators according to the present invention are most suitable for application using a multitude of intercalators and substituted intercalators which when combined with and functionalized by the various chains (T), where T is the chain comprised of R, $R_1$, $R_2$, $R_3$, $R_4$, W, X, Y and Z and bounded by the brackets in the previously discussed formulas, which provide high binding to DNA and RNA and lack of self-quenching and superior transport kinetics. Representative intercalators (I) are as follows:

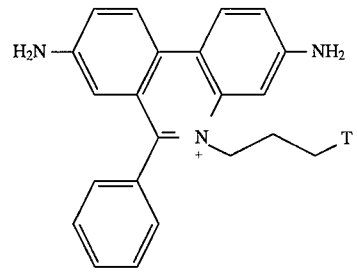

phenathridinium

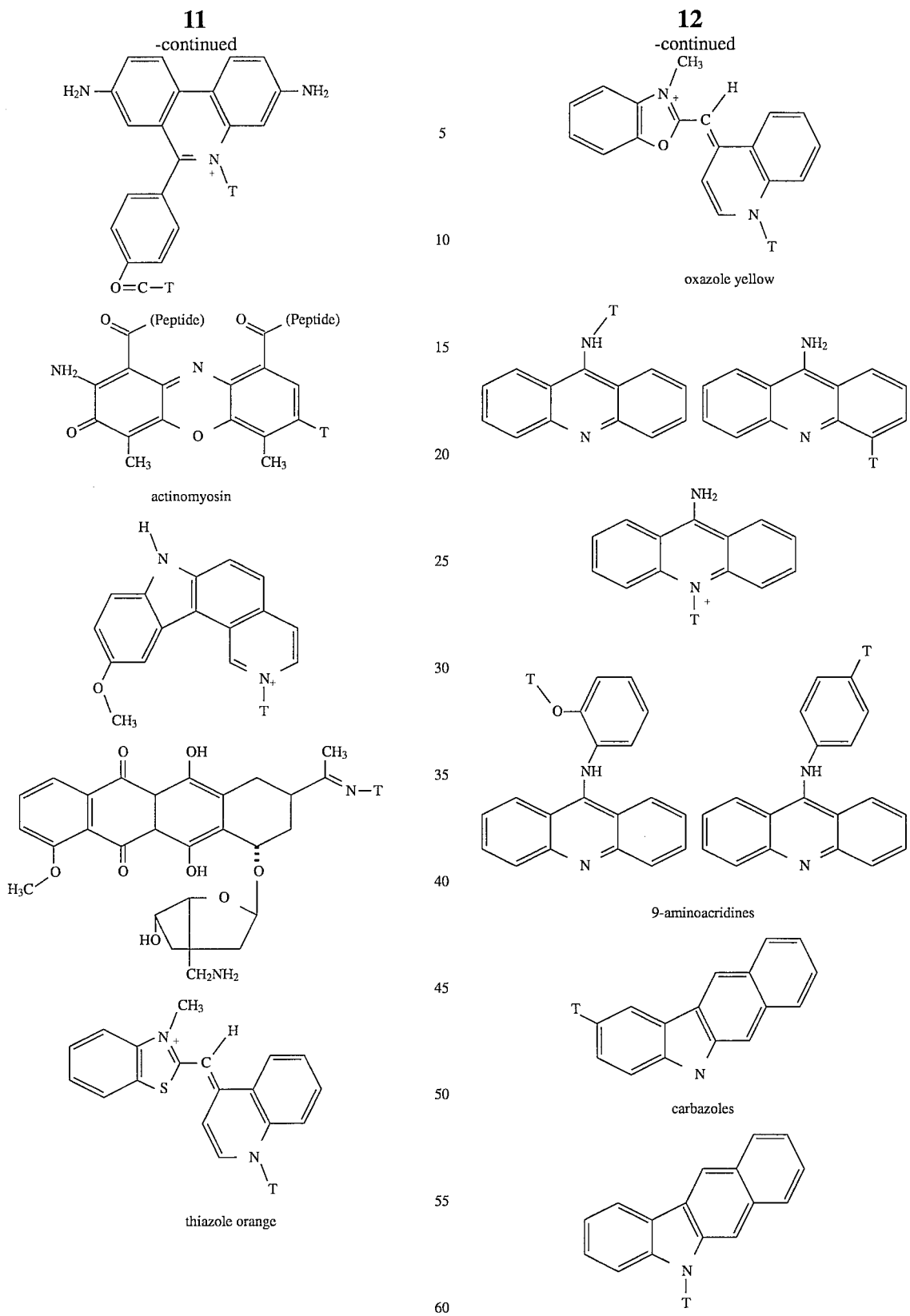

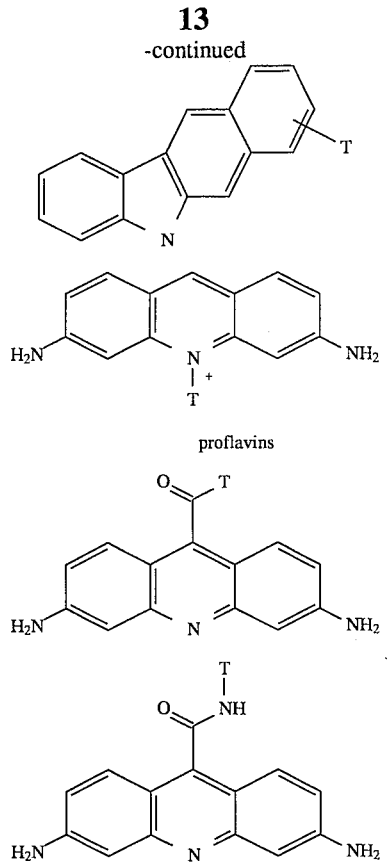

proflavins

DETAILED DESCRIPTION

Broadly, the present invention relates to a compound comprised of an intercalator or substituted intercalator segment derivatized with functionalized chains having high affinity for binding to a DNA molecule. More particularly, the invention relates to use of these intercalator compounds which exhibit improved binding to a DNA molecule within known methodologies requiring intercalator insertion into the DNA molecule. Still, the invention relates to enhanced binding of DNA molecules by an intercalator functioning segment utilized in labeling, capture, therapeutic insertion, assay and the like, with improved performance of the intercalator due to the increased utilization efficiency of the compounds. Improved binding to the DNA molecule of intercalators and substituted intercalators is achieved which exhibit high affinity for binding, reduced self-quenching, and superior transport kinetics, especially when compared to ethidium homodimer or other bis-intercalators.

The various embodiments of the present invention inclusive of synthesization of the compounds and utilization of said compounds are shown in FIGS. 1–9, 10A–10F, 11 and 12. The information shown in these figures clearly demonstrates high affinity for binding, reduced self-quenching, and superior transport kinetics, especially when compared to ethidium homodimer or other bis-intercalators.

FIG. 1 is a FACScan™ display for side scatter versus forward scatter (SSC on abscissa axis and FSC on the ordinate axis) for a typical distribution of white cells lysed with WBC DIL diluent with NRBC dye phenathridinium triamine V (PTA) and CEN. The quadrant thresholds were set to preclude the lymphocytes gated on the SSC versus FSC dot plot.

Figure 2:
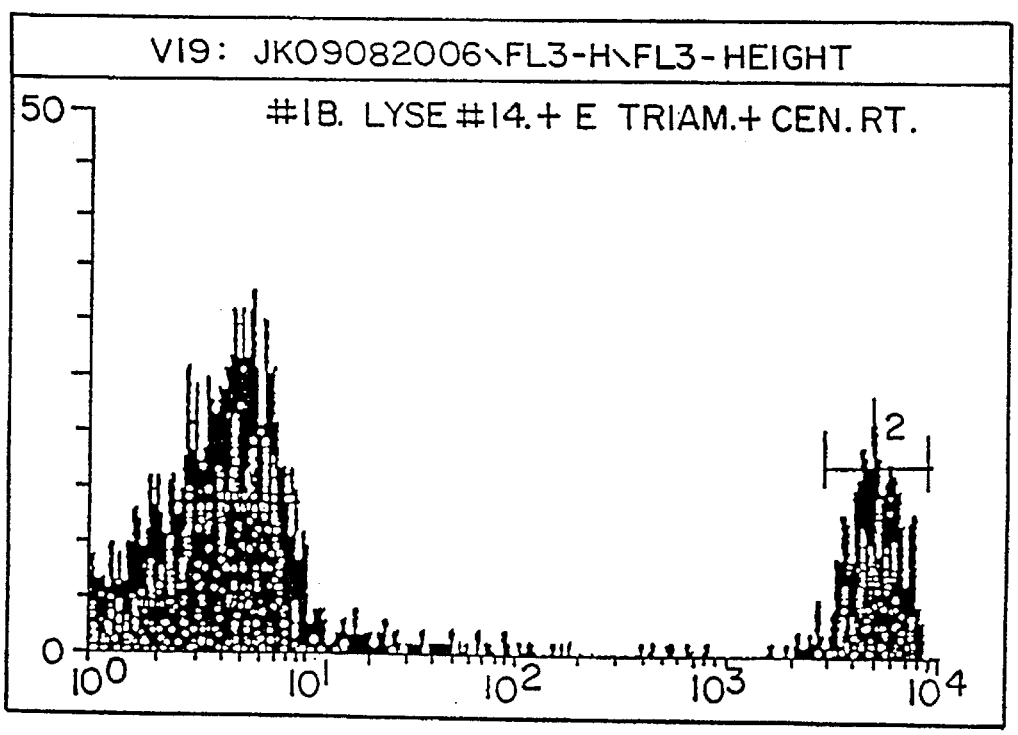
FIG. 2 is a histogram of fluorescence intensity (abscissa) versus frequency of events (ordinate).

FIG. 2 is a histogram of fluorescence intensity (abscissa) versus frequency of events (ordinate) for the populations of stained and unstained cells in the presence of phenathridinium triamine V (PTA).

Figure 3:
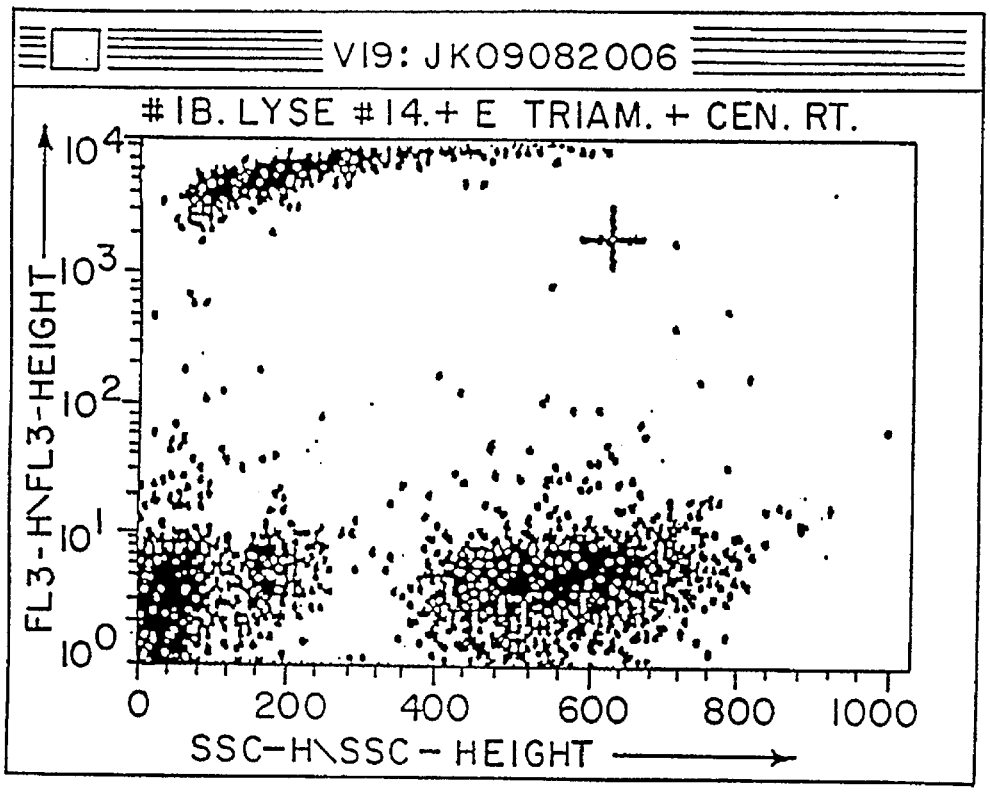
FIG. 3 is a scattergram representation for side scatter (SSC on abscissa) versus fluorescence intensity (ordinate).

FIG. 3 is a scattergram representation for side scatter (SSC on abscissa) versus fluorescence intensity (ordinate) showing the separation of cells stained with phenathridinium triamine V (upper left hand corner, NW quadrant) from unstained cells (remainder) by fluorescence intensity.

Figure 4:
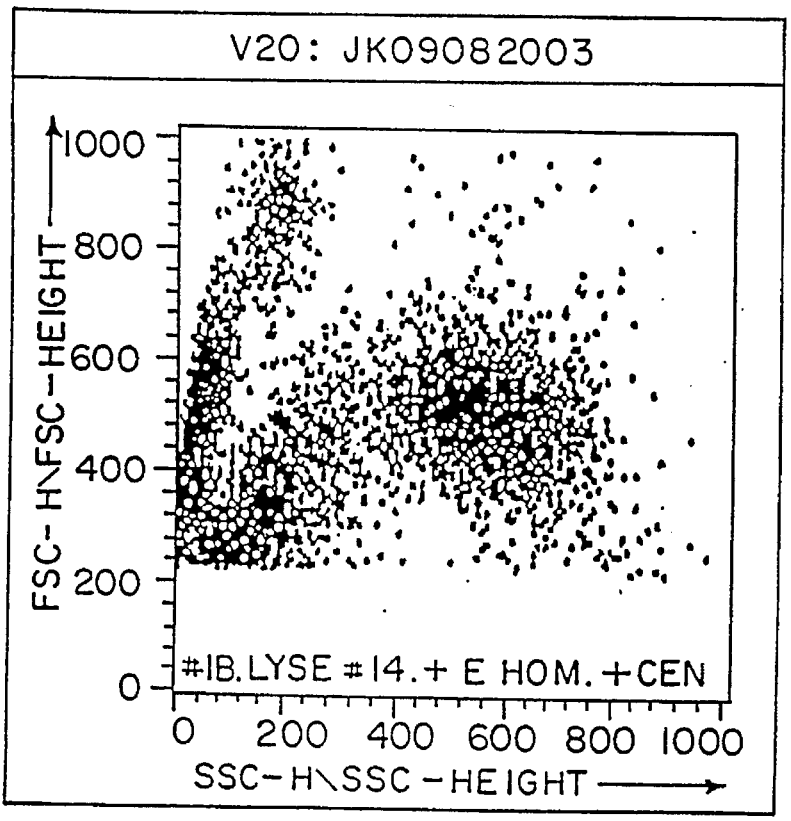
FIG. 4 is a FACScan™ display for side scatter versus forward scatter.

FIG. 4 is a FACScan™ display for side scatter versus forward scatter (SSC on abscissa axis and FSC on the ordinate axis) for a typical distribution of white cells lysed with WBC DIL diluent with NRBC dye ethidium homodimer and CEN. The quadrant thresholds were set to preclude the lymphocytes gated on the SSC versus FSC dot plot.

Figure 5:
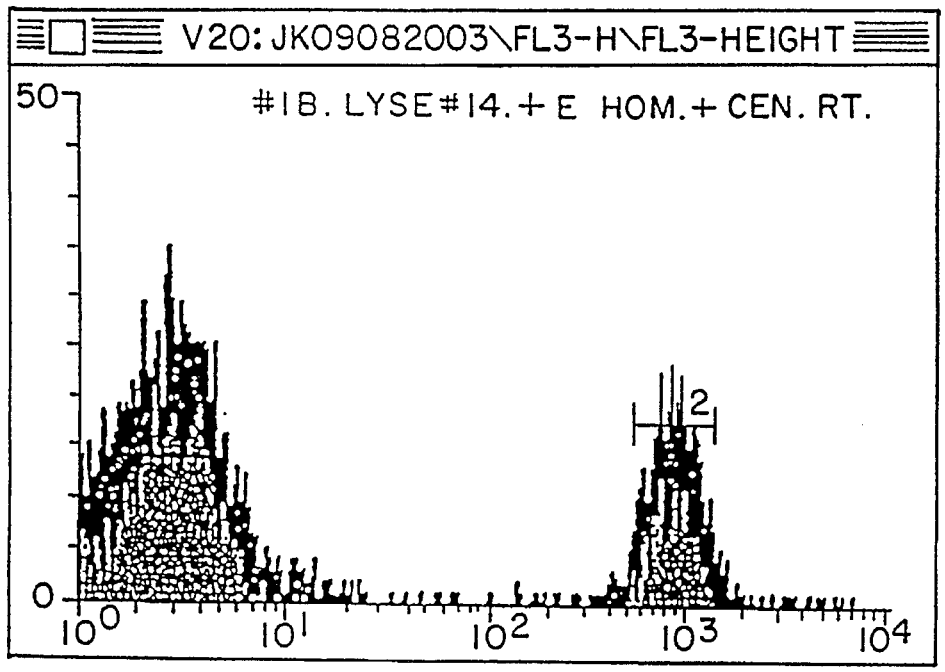
FIG. 5 is a histogram of fluorescence intensity (abscissa) versus frequency of events (ordinate).

FIG. 5 is a histogram of fluorescence intensity (abscissa) versus frequency of events (ordinate) for the populations of stained and unstained cells in the presence of ethidium homodimer.

Figure 6:
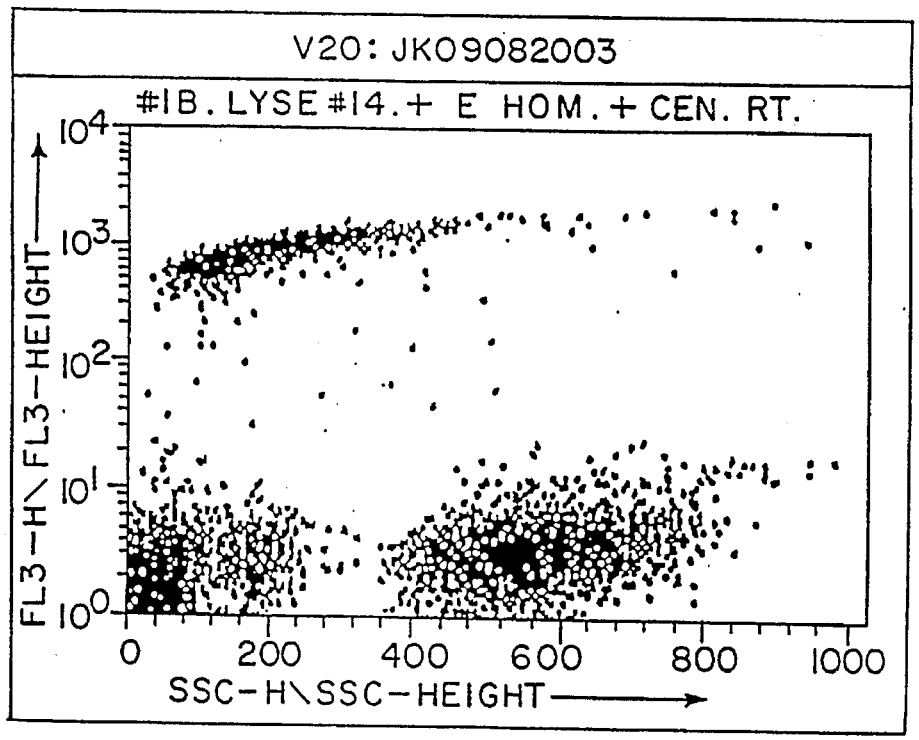
FIG. 6 is a scattergram representation for side scatter (SSC on abscissa) versus fluorescence intensity (ordinate).

FIG. 6 is a scattergram representation for side scatter (SSC on abscissa) versus fluorescence intensity (ordinate) showing the separation of cells stained with ethidium homodimer (upper left hand corner, NW quadrant) from unstained cells (remainder) by fluorescence intensity.

Figure 7:
FIG. 7 is a photographic representation of a UV light irradiated agarose electrophoresis gel performed on BAMH nicked PBR322 plasmid DNA.

FIG. 7 is a photographic representation of a UV light irradiated agarose electrophoresis gel performed on BAMH nicked PBR322 plasmid DNA. Loadings of 5 ul of stock solutions were made for lanes 3–14. The following stock solutions of DNA and intercalator were used to load lanes 1–14. Lane 1: marker; Lane 2: blank; Lane 3: 20 ng/ml 5plasmid stained with ethidium bromide; Lane 5: 160 pg/ml plasmid stained with ethidium bromide; Lane 6: 40 pg/ml plasmid stained with ethidium bromide; Lane 7: 20 ng/ml plasmid stained with ethidium homodimer; Lane 8: 800 pg/ml plasmid stained with ethidium homodimer; Lane 9: 160 pg/ml plasmid stained with ethidium homodimer; Lane 10: 40 pg/ml plasmid stained with ethidium homodimer; Lane 11: 20 ng/ml plasmid stained with PTA; Lane 12: 800 pg/ml plasmid stained with PTA; Lane 13: 160 pg/ml plasmid stained with PTA; Lane 14: 40 pg/ml plasmid stained with PTA. In all cases, the dye/base pair ratio was 1/20. In all cases, the dye was pre-incubated with the DNA and no post-gel-electrophoresis staining was done.

Figure 8:
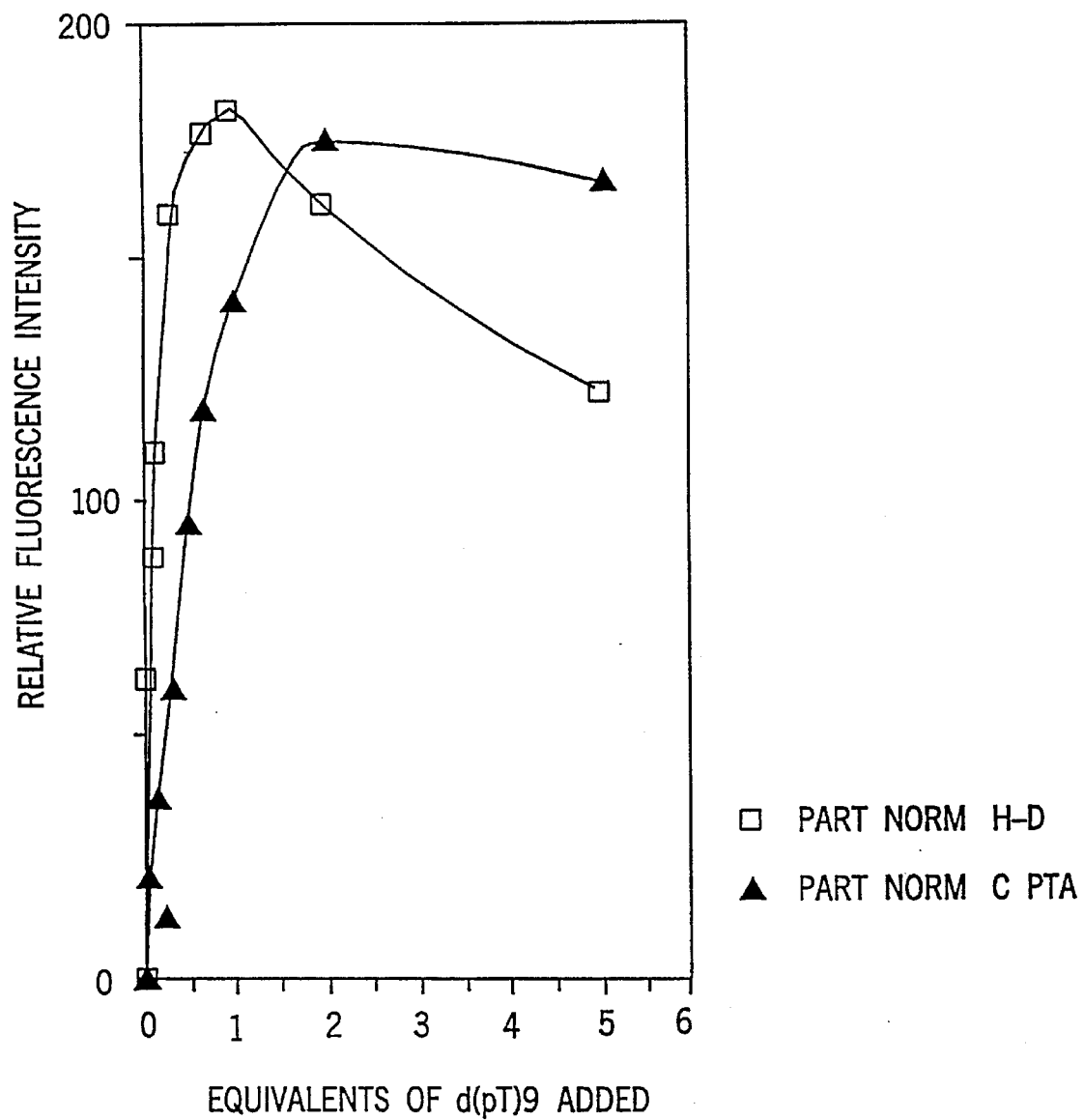
FIG. 8 is a hybridization saturation plot for equivalents.

FIG. 8 is a hybridization saturation plot for equivalents of d(pT)9 added to d(pA)9 at 6.6 micromolar DNA and 3.08 micromolar dye for ethidium homodimer and PTA V at a dye base pair ratio of 1:4. Graphical representation of equivalents of complementary oligonucleotide d(pT)9 on the abscissa added to d(pA)9 versus relative fluorescence intensity on the ordinate generated by using the protocol described in Example 2 to compare ethidium homodimer and phenanthridinium triamine V. The concentration of fluorophore in both cases was 3.08 micromolar using a two-fold statistical correction for the 2.0 molar equivalents of phenanthridinium moiety per each mole of ethidium homodimer. Both curves are normalized to background for relative fluorescence. Excitation was at 488 nm (534 nm is the excitation maximum) for this experiment and emission was at 625 nm.

Figure 9:
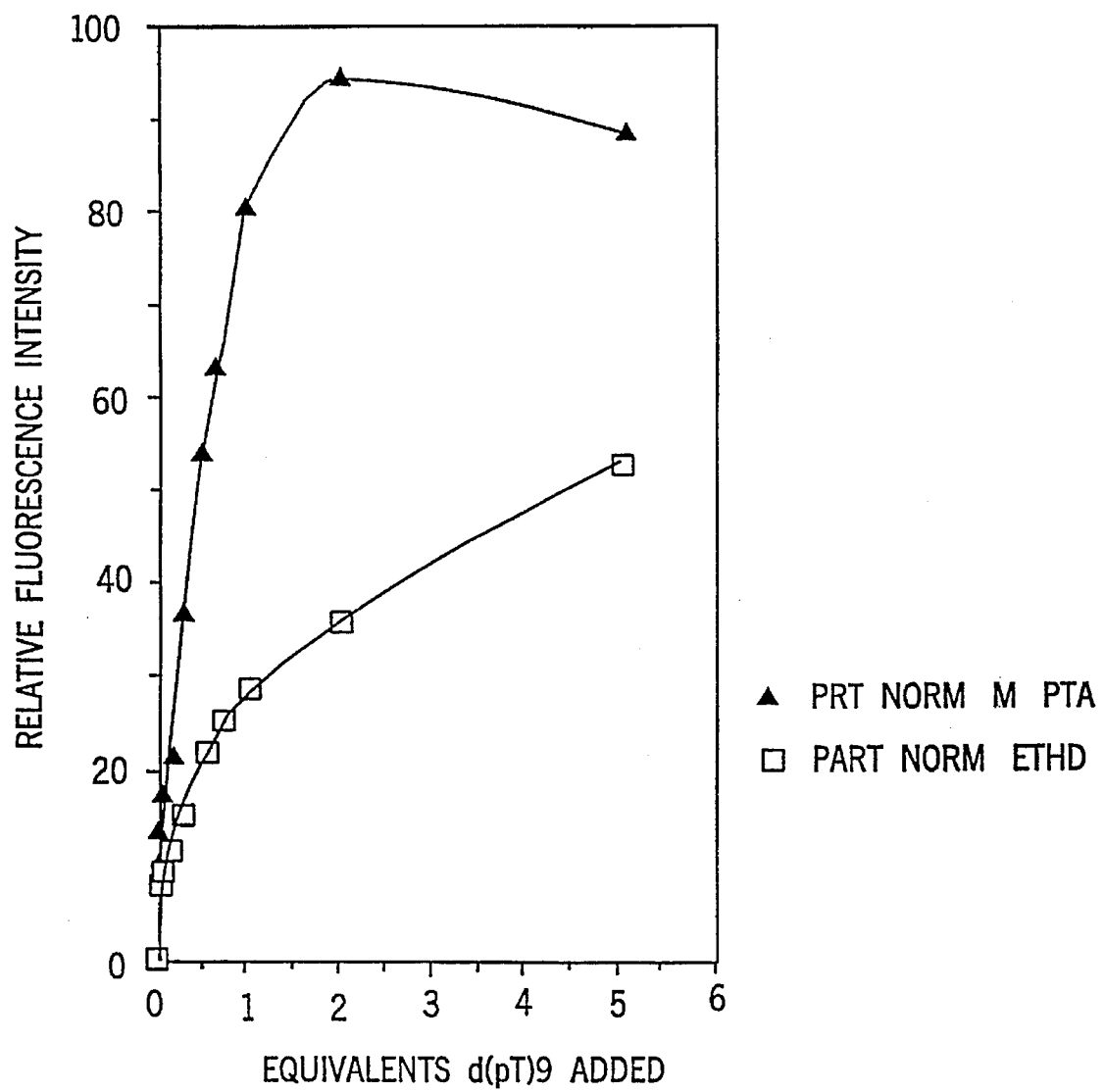
FIG. 9 shows hybridization titration curves for fluorescence intensity versus equivalents.

FIG. 9 shows hybridization titration curves for fluorescence intensity versus equivalents of d(pT)9 added to d(pA)9 at 6.6 micromolar DNA and 3.08 micromolar ethidium bromide and phenanthridinium triamine V. Graphical representation of equivalents of complementary oligonucleotide d(pT)9 abscissa versus relative fluorescence intensity (ordinate) generated by using the protocol described in Example 2 to compare ethidium bromide and phenanthridinium triamine V. The concentration of fluorophore in both cases was 3.08 micromolar. Both curves are normalized to background. Excitation was at 488 nm (534 nm is maximum excitation) and emission was at 625 nm and intensities were measured using a Hitachi F-3010 fluorimeter.

Figure 10A:
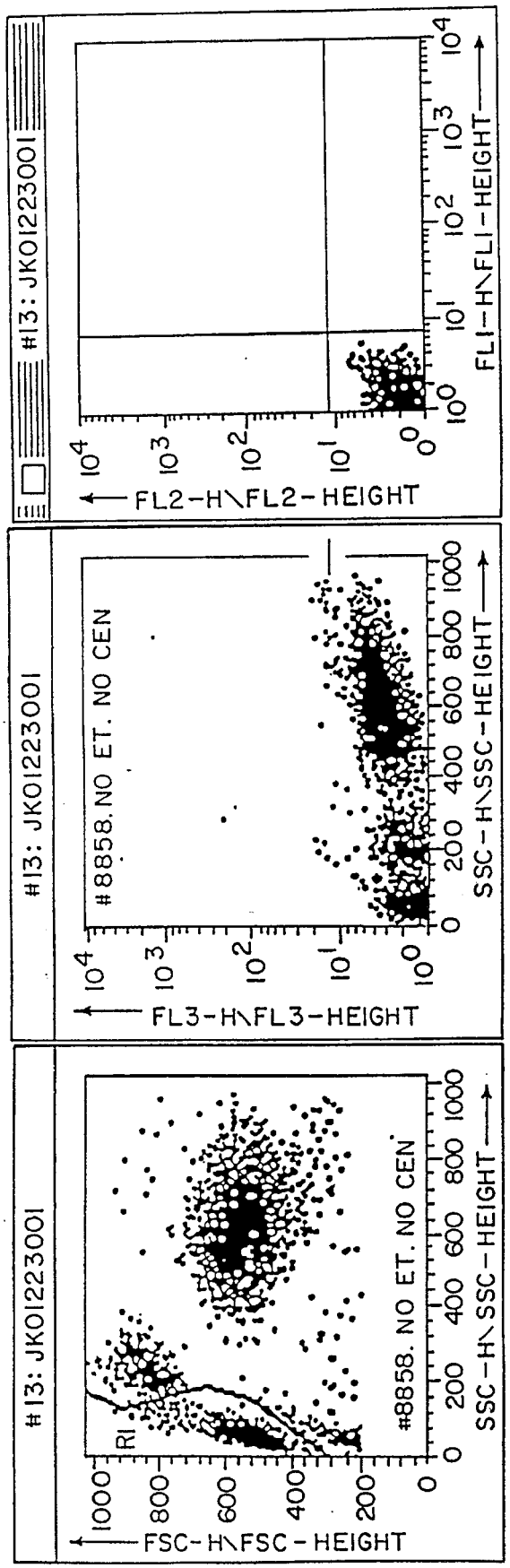
FIG. 10A is a FACScan™ display (SSC vs FSC) of a typical distribution of lysed white cells.

FIG. 10A is a FACScan™ display (SSC vs FSC) of a typical distribution of white cells lysed with CD4000 WBC DIL without NRBC dye or CEN. The quadrant thresholds were set to preclude the lymphocytes gated on the SSC versus FSC dot plot.

Figure 10B:
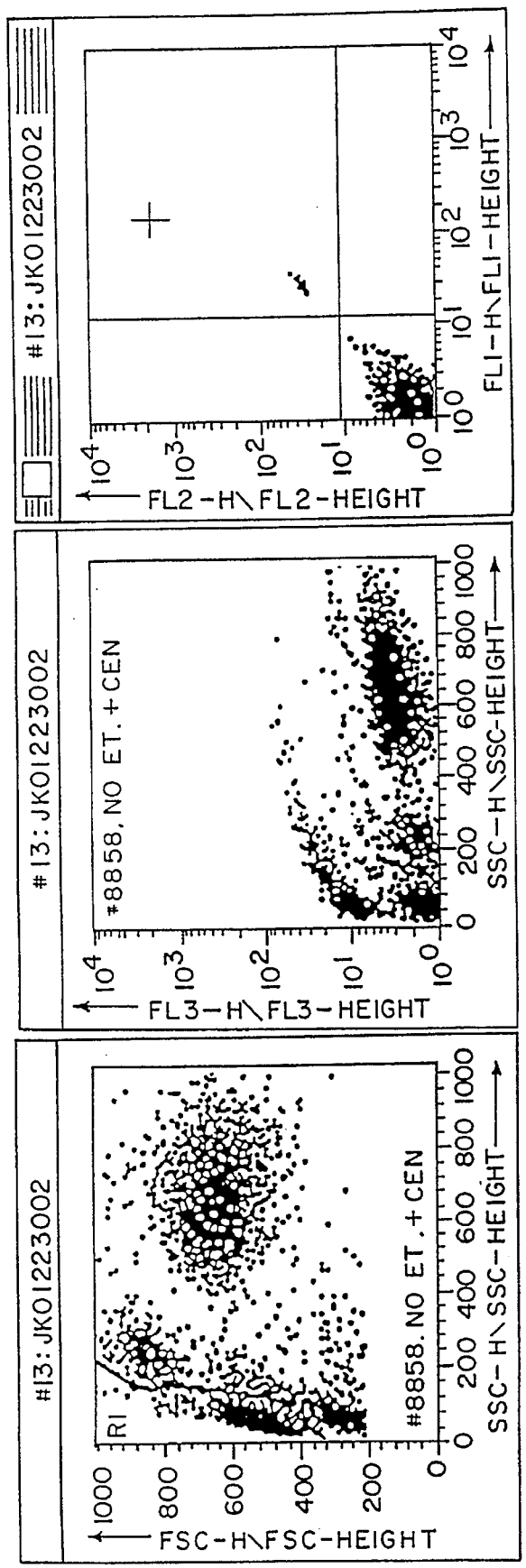
FIG. 10B is a FACScan™ display of the same blood sample as in FIG. 10A with unstained CEN added.

FIG. 10B is a FACScan™ display of the same blood sample as in FIG. 10A with unstained CEN added. As can be seen, the unstained CEN demonstrate some FRL3 autofluorescence. The region 1 was set to include all FL3+ events in this unstained sample, so that stained cells in the test samples can be counted in the region 2. The region 3 is set to include the CEN population only to measure the mean FL3 of the population.

Figure 10C:
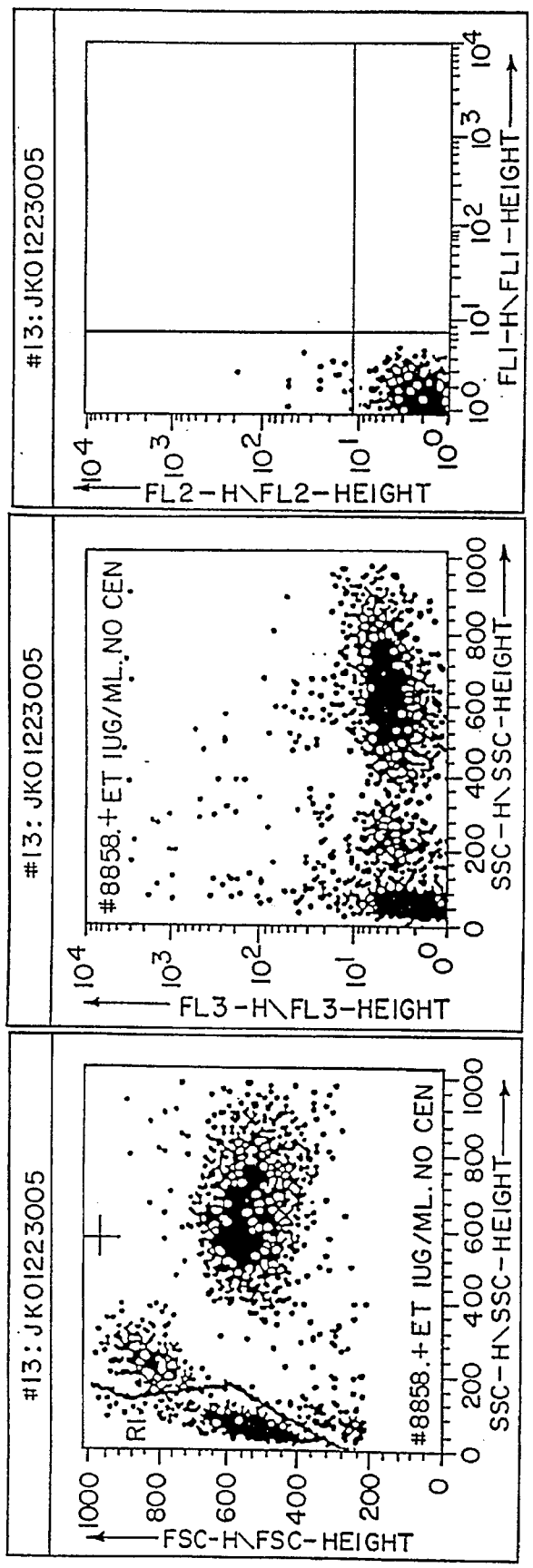
FIG. 10C is a FACScan™ display of the same sample lysed with WBC DIL.

FIG. 10C is a FACScan™ display of the same sample lysed with WBC DIL containing 1.0 ug/ml of NRBC dye. 1.3% of FL2+ events were detected in UL from the gated lymphocytes and 1.08% of FL3+ events are detected from the ungated total white cell population.

Figure 10D:
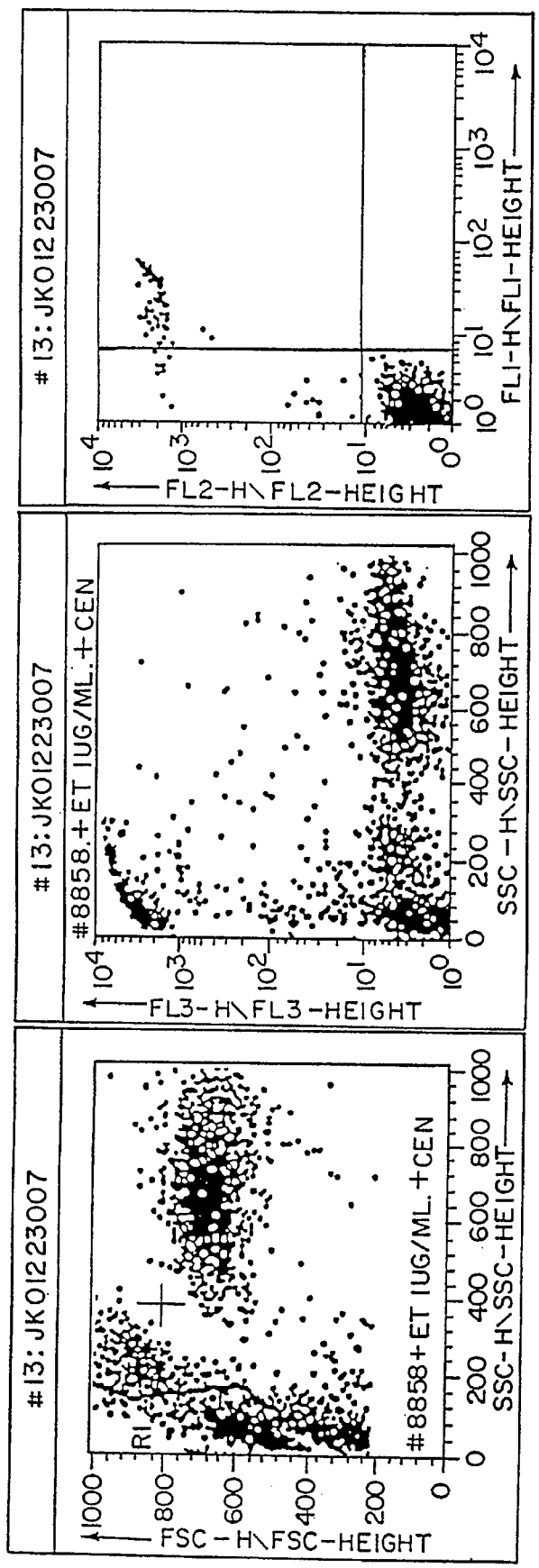
FIG. 10D is a FACScan™ display of the same sample as presented in FIG. 10C, but with CEN.

FIG. 10D is a FACScan™ display of the same sample as presented in FIG. 10C, but with CEN. The region 2 of the FL3 histogram of the ungated population shows the stained CEN population which has the mean FL3 of 3319.8.

Figure 10E:
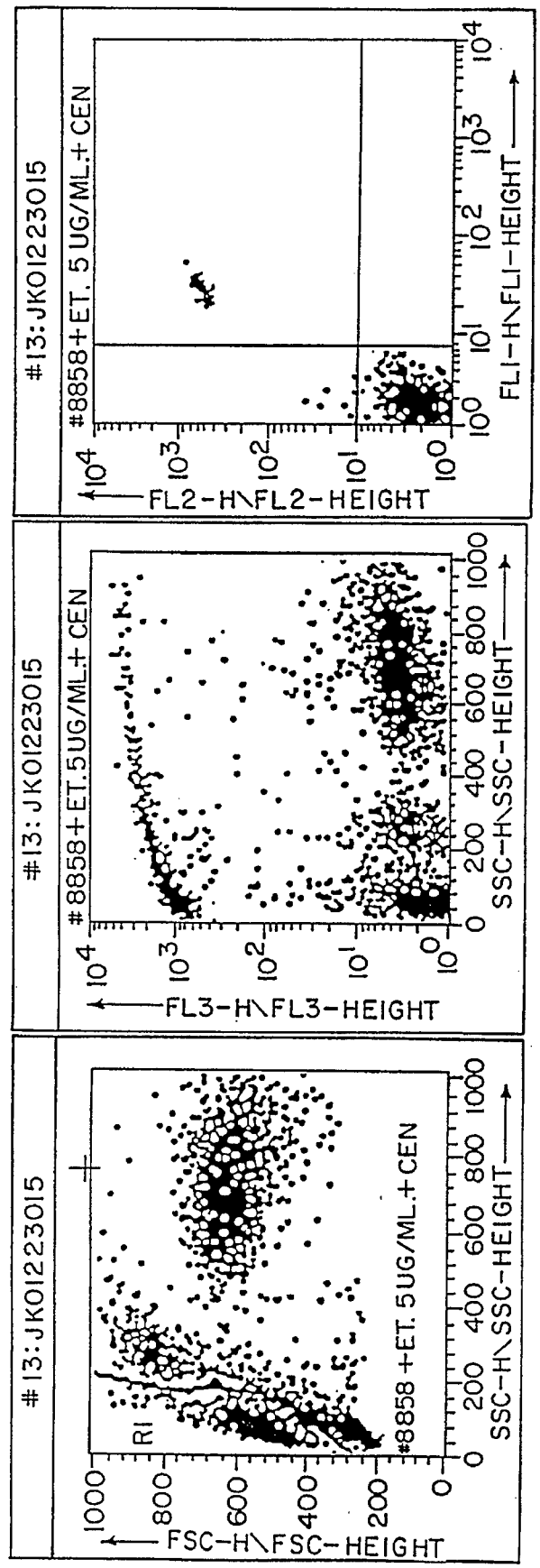
FIG. 10E is a FACScan™ display of the same sample lysed in the same diluent as FIG. 10D, but with 0.5 ug/ml of NRBC dye.

FIG. 10E is a FACScan™ display of the same sample lysed in the same diluent as FIG. 10D, but with 0.5 ug/ml of NRBC dye.

Figure 10F:
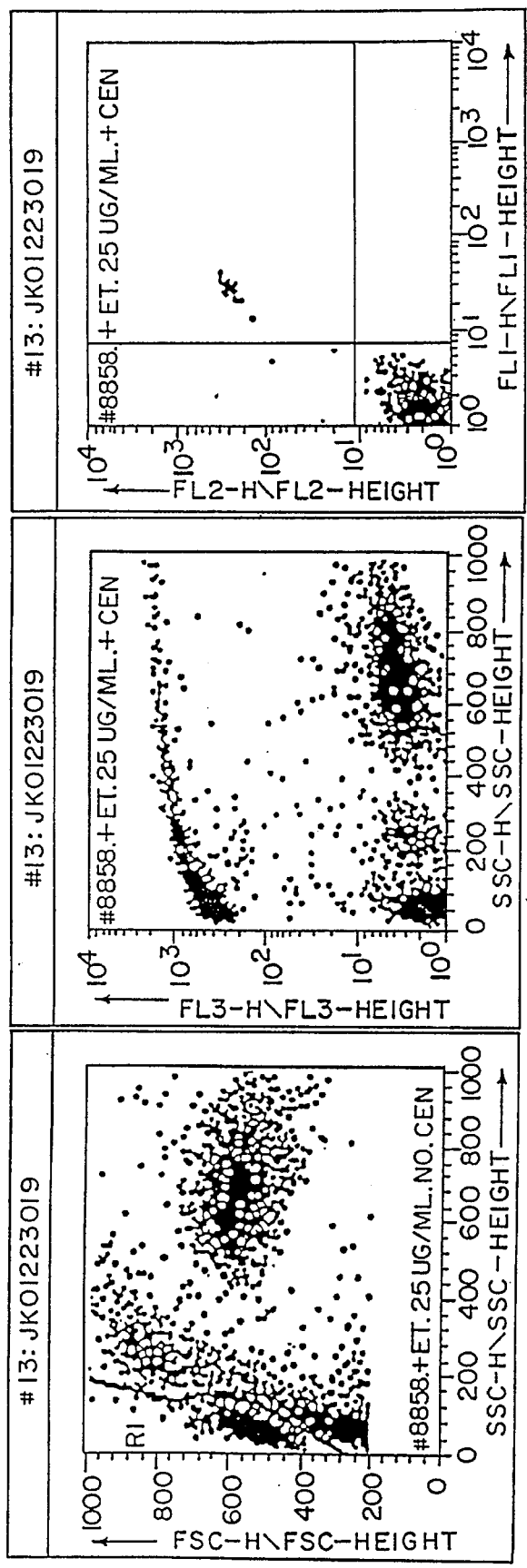
FIG. 10F is a FACScan™ display of the same sample lysed in the same diluent as FIG. 10D, but with 0.25 ug/ml of NRBC dye.

FIG. 10F is a FACScan™ display of the same sample lysed in the same diluent as FIG. 10D, but with 0.25 ug/ml of NRBC dye. As can be seen, the stained CEN is still well separated from the white cells.

Figure 11:
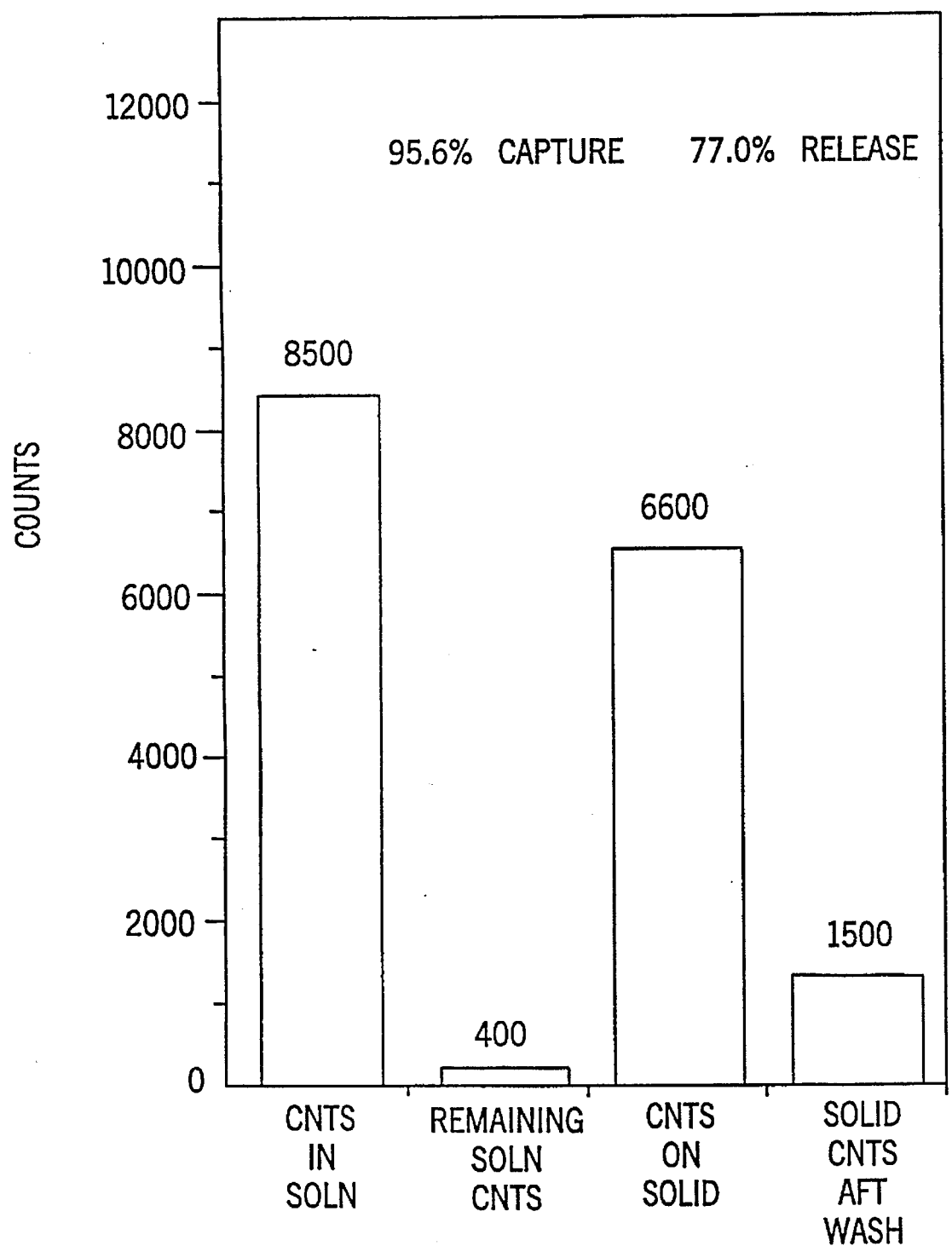
FIG. 11 is a graphical representation of the efficiency of 32P radiolabelled, restriction enzyme-nicked plasmid DNA capture onto phenathridinium activated polystyrene microparticles synthesized as described in Example 6.

FIG. 11 is a graphical representation of the efficiency of 32P radiolabelled plasmid DNA capture onto phenanthridinium activated polystyrene microparticles synthesized as described in Example 6. A: initial radioactive counts in solution accounting for the total DNA concentration; B: radioactive counts remaining in solution after removal of DNA via centrifugation as described in Example 6; C: initial radioactive counts on the DNA bound to the microparticle by the phenthridine moiety before release is initiated by NaOH; and D: radioactive counts remaining on the solid after removal of DNA with NaOH.

Figure 12:
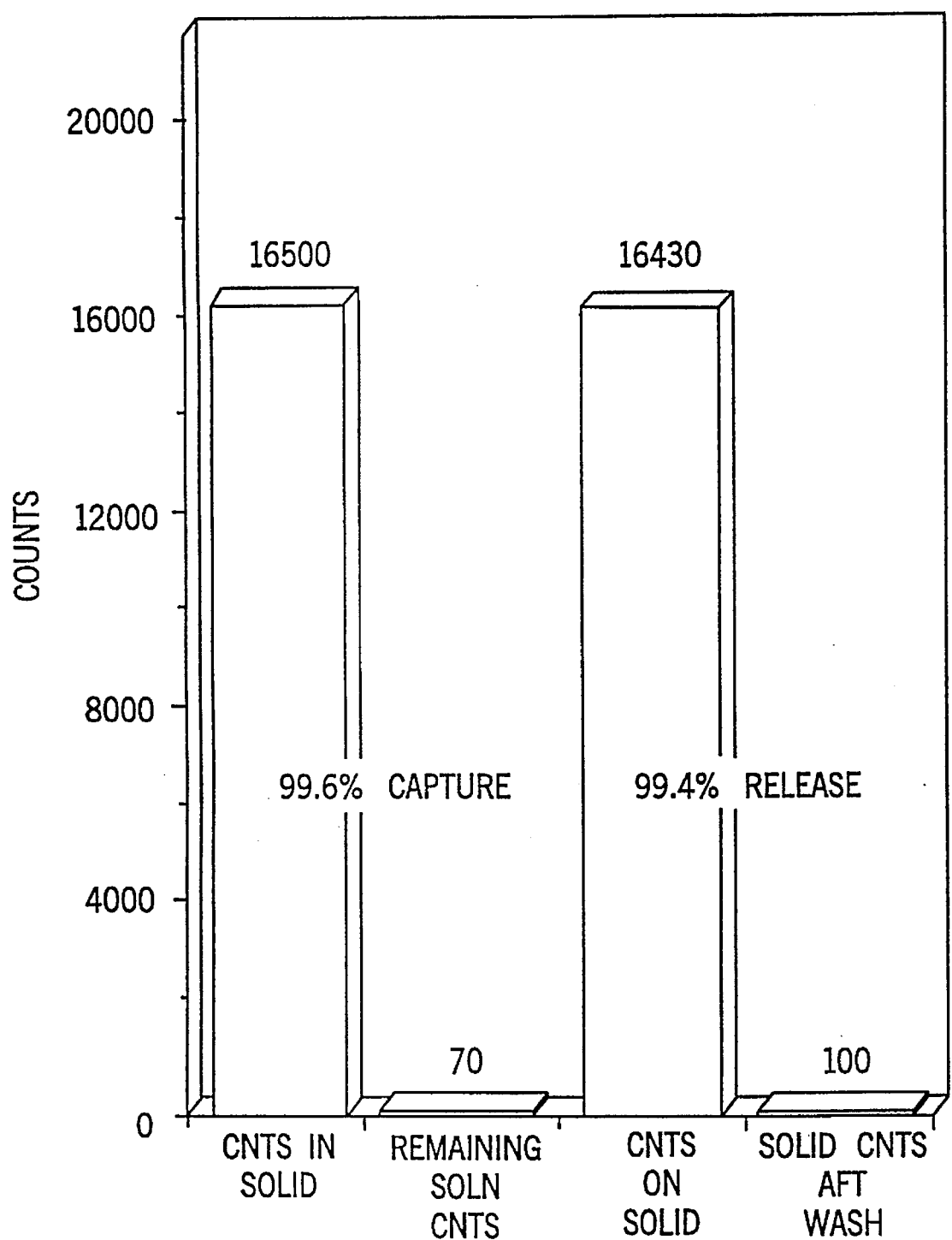
FIG. 12 is a graphical representation of the efficiency of 32P radiolabelled plasmid DNA capture onto phenathridinium activated carboxymethyl sepharose beads synthesized as described in Example 6.

FIG. 12 is a graphical representation of the efficiency of 32P radiolabelled plasmid DNA capture onto phenanthridinium activated carboxymethyl sepharose beads synthesized as described in Example 6. A: initial radioactive counts in solution accounting for the total DNA concentration; B: radioactive counts remaining in solution after removal of DNA via centrifugation as described in Example 6; C: initial radioactive counts on the DNA bound to the microparticle by the phenthridine moiety before release is initiated by NaOH; and D: radioactive counts remaining on the solid after removal of DNA with NaOH.

The invention is further defined by the following Examples, which provide basis for the FIGURES and are intended to be illustrative, but not limiting.

EXAMPLE 1

Synthesis of Phenanthridinium Triamine V (PTA) And Precursor Intermediates I–IV

Product V, a compound according to the invention, was synthesized through the sequence shown in the following schematic. The experimental procedures used to obtain product V are as illustrated therein. Intermediate I. Commercially available from Aldrich Chemical Co. Intermediate II. Starting material I, 3,8 Diamino 6-phenyl phenathridine (25.0 g, 0.0876 moles), was obtained from the Aldrich Chemical Company (Milwaukee, Wis.) and added to a single neck 3.0 liter round bottom flask under Argon and equipped with a magnetic stir bar and a reflux condenser. To this vessel, 1.0 liter of dry pyridine was added while stirring. Stirring of the resulting suspension was continued for 15 minutes until all the solid had dissolved. A catalytic amount of N,N-dimethylaminopyridine (1.07 g, 0.0086 moles) was added to this solution while stirring. Acetic anhydride (462 g, 4.9 moles) was then added and the resulting reaction mixture was refluxed for 8–12 hours. The reaction mixture was then allowed to cool and the solvent was removed in vacuo. For purification of the Product II, a gradient silica gel column was performed using 2.0 liters of 45/40/10/5 Ethyl acetate/hexane/$CH_2Cl_2CH_3OH$ followed by 1.0 liter of 40/40/10/10 EtOAc/hexane/$CH_2Cl_2$/$CH_3OH$. Fractions of 10.0 ml were collected and appropriate fractions were recombined and the solvent was removed in vacuo. The sticky gum-like residue was then dissolved in hot EtOH (220 ml) and precipitated by cooling to 0° C. The mother liquor was decanted off and 200 ml of fresh EtOH was added. The solid was redissolved by heating and allowed to crystallize at −4° C. for 48 hours. Crystals were collected from both the mother liquor and the second recrystallization and were washed with a small amount of cold EtOH and dried under high vacuum for several hours. Isolated yield of pure product after column chromatography and two recrystallizations was 32%. $^1$H NMR CD3OD (300 MHz) 9.1 (d, 1H 8.82 Hz), 9.0 (d, 1H, 8.75 Hz), 8.08 (s, 1H), 7.95 (s, 1H), 7.92 (d, 1H, 4.5 Hz), 7.8 (m, 3H), 7.65 (m, 3H), 2.45 (s, 6H), 2.35 (s, 6H); $^{13}$C NMR $CD_3OD$ (75.45 MHz) 174.5, 163.7, 145.3, 142.1, 140.6, 139.9, 134.4, 133.8, 130.8, 130.6, 129.8, 127.3, 125.9, 125.6, 124.8, 27.1, Exact Mass Calc. for $C_{27}H_{23}N_3O_4$, Calc. 453.1688 exact mass, Obs: 453,1683; CH analysis Calc for $C_{27}H_{23}N_3O_4$ C: 71.51 H: 5.11 N: 9.27 Found C: 71.77 H: 5.10 N:9.20. Intermediate III. Intermediate III was synthesized from the diamine II via a modification of a literature procedure (GaGaugain et al., Biochemistry, Vol. 17, o. 24, 1978, pp. 5071–5078) for quarternization of the diamide of 3,8 Diamino-6-phenyl phenanthridine. Diamide II (10.5 g, 0.023 moles) was placed in a 2.0 liter round bottom flask under argon and equipped with a magnetic stir bar and reflex condenser. 1,3 Dibromopropane (1.0 liter, 9.86 moles) was added to this flask and the resultant mixture was brought to reflux for 7 hours. The solution was cooled overnight and the precipitant was filtered and washed with diethyl ether. Obtained 10.44 g (68.7%) of crude material III. This material was recrystallized from $CH_3OH$ to yield 5.3 g of diacetyl bromide III. $^1$H NMR $CD_3OD$ (300 MHz) delta 10.75 (s, 1H), 10.45 (s, 1H), 9.3 (s, 1H), 9.09 (d, 9.2 Hz, 1H), 9.04 (d, 9.2 Hz, 1H), 8.45 (d, 9.1 Hz, 2.2 Hz, 1H), 8.12 (s, 1H), 8.07 (d 9.0 Hz, 1H), 7.95 (m, 3H), 7.85 (m, 3H), 5.0 (t, 9.0 Hz, 3H), 3.6 (t, 6.0 Hz, 2H), 2.65, 2.38 7.75 $^{13}$C NMR 26DMSO (75.45 MHz) delta 169.9, 169.3, 163.8, 142.1, 139.9, 134.2, 131.5, 130.5, 129.5, 128.4, 125.9, 125.4, 123.6, 122.3, 121.6, 119.0, 107.7, 55.7, 30.7, 24.5, 24.2; exact mass Calc. for $C_{26}H_{29}N_3O_2Br_2$ free salt (FAB+) 490.1131 Obs: 490.1139; CH analysis Calc. for $C_{26}H_{29}N_3O_2Br_2$ H: 4.41 C: 54.66 N:7.36 Found H: 4.25 C: 54.65 N: 7.30. Intermediate IV. III (5.3 g, 0.0081 moles) was added to a 250 ml round bottom flask equipped with a magnetic stir bar and reflux condenser. Methanol (150 ml) was then added to this flask while stirring under nitrogen and diethylene triamine (29.2 g, 0.283 moles) was added while stirring was continued. The resultant transparent solution was heated to reflux overnight under nitrogen. This solution was then allowed to cool to room temperature and poured into distilled $H_2O$. Then this mixture was concentrated in vacuo until only the $H_2O$ remained. An additional 50–75 ml $H_2O$ was added and the solution was allowed to cool to 0° C. The solid was then filtered and washed with ice cold water. This material was then redissolved in EtOH and precipitated with 10N HCl. After filtration of the suspension, the resultant solid was recrystallized from hot ethanol upon cooling to 0° C. for 15 minutes. A second crop was also collected from the second filtrate upon standing and by precipitation with EtOH from the first filtrate. These solids were then combined and the final product IV (2.5 g) was obtained after high vacuum overnight. $^1$H NMR CD$_3$OD (300 MHz) delta 9.2 (s, 1H), 9.05 (d, 1H), 8.95 (d, 1H), 8.4 (broad s, 2H), 8.3 (broad s, 1H), 7.9 (broad m, 3H), 7.7 (broad m, 2H), 5.1 (broad m, 1H), 3.9 (broad s, 3H), 3.45 (broad m, 2H), 3.85 (broad m, 2H), 2.5 (broad m, 3H), 2.3 (broad m, 3H); MS Calc. for free salt $C_{30}H_{37}N_6O_2$(FAB+) 513 Obs: 513.

Product V. Synthesis and purification of the phenanthidinium triamine, PTA, V was accomplished by the following protocol. Triamine IV (2.35 g, 0.0036 moles) was dissolved in 75.0 ml methanol and 75 ml of 4N HCl was added. The mixture was refluxed for 2 hours and allowed to cool. Ethanol was added to this solution and resulting precipitate was filtered and washed with a minimal amount of cold ethanol. The filtrate was reconcentrated and fresh ethanol and concentrated aqueous HCl was added. This resulting precipitate was also filtered. Next, this filtrate was concentrated to near dryness and Et2O was added and the solid filtered off. The last remaining unfilterable residue was then dissolved in concentrated HCl and precipitated with EtOH. This material was filtered and washed with ethanol, combined all solid materials from the above sequence and subjected this material to high vacuum overnight to obtain 2.03 g total of the high affinity fluorescent DNA stain phenathridium triamine V (PTA). $^1$H NMR d$_6$-DMSO (300 MHz) delta 10.0 (broad s, 2H), 9.65 (broad s, 2H), 8.68 (d, 14.2 Hz, 2H), 8.35 (broad s, 2H), 7.75 (m, 4H), 7.65 (s, 1H) 7.55 (d, 9.2 Hz, 2H), 7.35 (d, 9.2 Hz, 2H), 6.28 (s, 1H), 4.5 (broad s, 2H), 4.0 (broad s, 8H), 3.4 (broad s, 2H), 3.0 (broad s, 2H), 2.3 (broad m, 2H); 13C NMR d$_6$-DMSO (75.45 MHz) δ159.7, 151.1, 134.6, 131.7, 130.9, 129.4, 128.8, 128.4, 124.9, 122.9, 120.1, 117.4, 99.6, 51.4, 43.8, 42.5, 40.3, 34.9, 18.5; High resolution mass spec. C26H33N6(FAB+) Calc. 429.2767, Obs: 429.2766; CH analysis Calc for C26H37N6C14.3H2O was H 6.89 C 49.61 N 13.35 Found H: 6.16; C 49.74 N: 13.08.

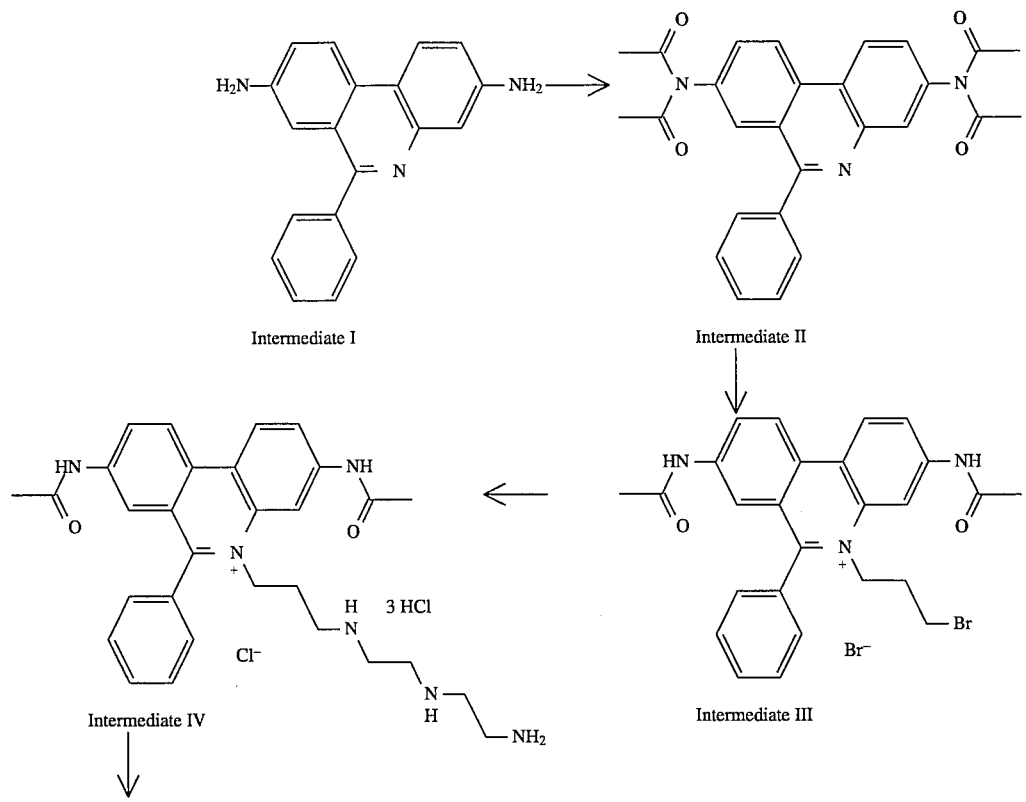

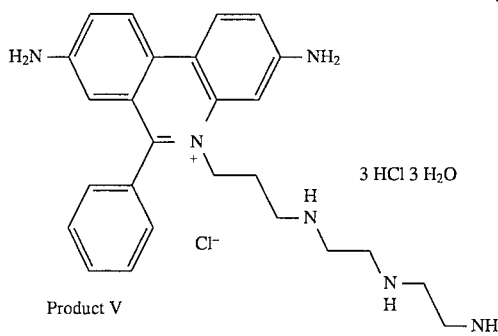

Product V

EXAMPLE 2

Hybridization Assay

Phenathridium triamine V (PTA) was used to quantitate hybridization when a target oligonucleotide was titrated with its complementary partner. A comparison of ethidium bromide staining versus PTA for detecting this hybridization, as per the following protocol, can be found in FIG. 9 and the comparison of ethidium homodimer versus PTA, as per the following protocol, can be found in FIG. 8. Complementary strands of DNA (oligodeoxythymidylic acid, $d(pT)_9$ and oligodeoxyadenylic acid $(d(pA)_9)$ were obtained from the Sigma Chemical Co. in St. Louis, Mo. A stock solution of d(pA)9 was made at 5 units/ml of 0.05M TRIS, 0.2N NaCl, 1 MM EDTA, pH 8.4. For polyA, $\epsilon=8.4$ AU/mM cm or 8,400 $M^{-1}cm^{-1}$; therefore, with 9 base pairs for d(pA)9, the $\epsilon$ is 75,600 $M^{-1}cm^{-1}$. This stock was then diluted 10× to obtain stock at $6.61\times10^{-6}M$, or 6.6 μM. The $d(pT)_9$ stock was made at 25 units/5.0 ml and used for filtration without further dilution in the same buffer. Since the (E for polyT is 8.15 AU/mM cm or 8,150 M–1 cm–1 per base pair, or 73,350 M–1cm–1 per oligo, the concentration of the oligo stock was 68 μM in DNA molecules. A titration was performed using a Hitachi F-4010 Fluorescence Spectrophotometer equipped with 0.5 ml microcells to obtain fully corrected spectra and an excitation wavelength of 488–550 nm (optimal around 534) and an emission wavelength of 600–650 nm (optimal around 25). Equivalents of $d(pT)_9$ were added at the following increments: 0.02, 0.05, 0.080, 0.150, 0.300, 0.500, 0.700, 1.00, 2.00, 5.00 equivalents. Each sample in the titration curve was prepared individually by dividing the initial d(pA)9 stock into 10×1.0 ml aliquots. The addition of complement was then accomplished by micropipetting an appropriate amount (2, 5, 8, 15, 30, 50, 70, 100, 200, and 500 μl, respectively) of d(pT)9 stock to each of a series of the 10 aliquots. Each aliquot, obtaining progressively larger molar ratios of the two complementary strands, was incubated at ambient temperature for 15 minutes, the dye was added as 20.0 μl aliquots of a 154 μM solution of the dye in 0.05M TRIS, 0.2N NaCl, 1 mM EDTA, pH 8.4 buffer. This corresponds to a dye/DNA b.p. ratio of 1/20 at saturation with complementary oligo. Overall concentrations of dye and oligo vary in the saturation plot because of the use of varied increments additions from the same stock solution. After an additional 15 minute incubation time, the relative fluorescence intensity was then read at 625 nm and recorded to generate a standard curve which is directly proportional to the quantity of dsDNA hybridization, or target sequence, under these conditions.

EXAMPLE 3

Gel Electrophoresis Application

An agarose gel was run to compare the staining intensity of ethidium bromide (Aldrich Chemical Co., Milwaukee, Wis.), HOMODIMER (Molecular Probes, Eugene, Oreg.), and PTA stain. Plasmid, $pBR_{322}$, at 2.1 mg in 7 ml stock was incubated at 37° C. for 1 hour with 1 ml of BAMH restriction enzyme with 2 ml 10× React2 Buffer and diluted to 20 ml total with 10 ml $H_2O$. This mixture was then used to prepare 3 stocks of nicked $pBR_{322}$ plasmid at 0.63 mg per 6 ml for each vial. Each of these stocks were diluted further with H2O and 20% glycerol to final DNA stocks of 20 ng/ml, 800 pg/ml, 160 pg/ml, and 40 pg/ml with a 1:4 ratio of dye to DNA base pairs in each for a total of 12 stocks. A 5 μl aliquot of each stock was loaded into 12 separate lanes in agarose gel and electrophoresis was run for 30 minutes in 4 mM TRIS, $pH_{8.2}$, with 0.01 mM EDTA buffer. The gel was then removed and photographed under exposure to U.V. light in a conventional gel box.

EXAMPLE 4

EXProtocol for Synthesis of Intercalator Activated Carboxymethyl Styrene Microparticle Capture Reagent The synthesis of intercalator derivatized solid phase microparticle (MP) capture reagent was accomplished by the scheme depicted in the following schematic and effected by the following procedure:

A 45 aliquot of 0.275±μm microparticles (Seradyne, Indianapolis, Ind.) were placed in a 4 ml vial and the surfactant was exchanged out using Bio-Rex 501-D ion exchange mixed bed resin (Bio-Rad, Richmond, Calif.). After gentle shaking for 2 hours, the resin was filtered out from the mixture by using a coarse fritted glass funnel equipped with a reduced pressure collection chamber. The sample was diluted to a concentration of mp at 10% solids by weight. The total amount of equivalents of reactive carboxylic acid were calculated from the titration specifications of the vendor. A stock solution of sulfo N-hydryoxysuccinimide (Pierce, Rockford, Ill.) was made at 11 mg/ml (20 mM) in $H_2O$ and a stock solution of EDAC (Sigma Chemical Co., St. Louis, Mo.) at 10 mg/ml (5 mM) was made in H2O. Five equivalents of EDAC (290 μl stock) was added to the carboxymicroparticle reaction mixture, followed by 5.0 equivalents of sulfo N-hydroxysuccinimide (330 μl stock). This mixture was allowed to incubate at room temperature for 2 hours and then a 2.0 molar equivalent of PTA dye (4 mg) was added at a concentration of 8 mg/400

μl, or 2.0 mg/100 μl in pH 8.0 0.1N NaCl 0.1N Pi phosphate buffer. N-hydryoxysuccinimide (Pierce) can be substituted for sulfo N-hydryoxysuccinimide if it is first dissolved in a stock of DMF (Dimethyl formamide) and aliquoted as described above. After allowing 24 hours for complete reaction, the free dye was then removed by centrifugation, removal of mother liquor, and resuspension for several attempts until the solution went clear and no more dye was extracted from the samples. The purified capture reagent was then diluted to a stock of 2–4% solids in $H_2O$.

stock was prepared at 10% solids in H2O. Note that controls were run with PTA modified and non-modified solid phases and minimal non-specific capture of DNA occurred with the underivatized materials.

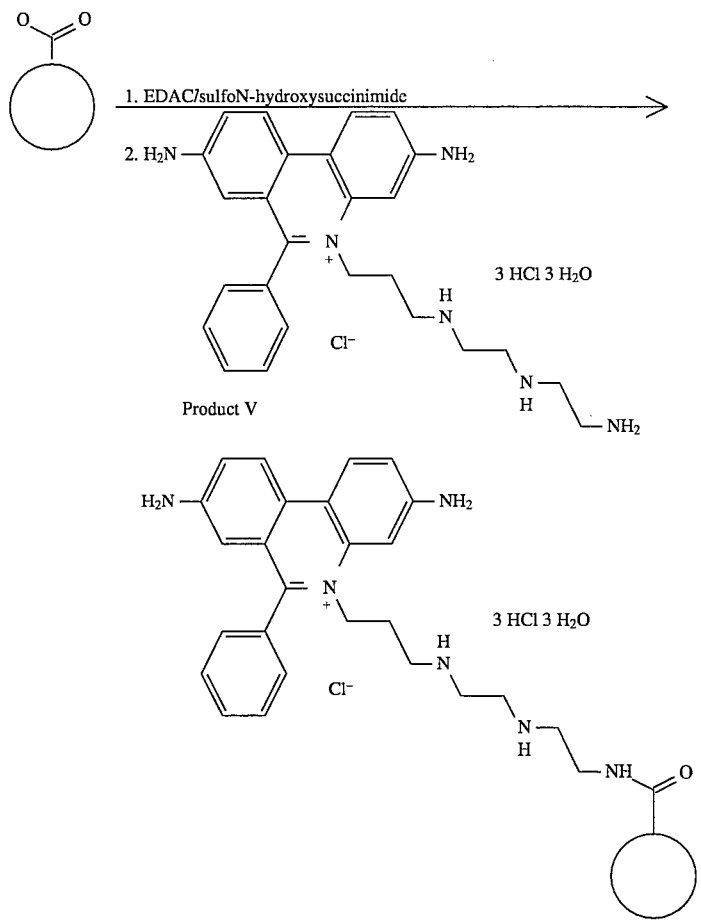

EXAMPLE 5

Solid Phase DNA Capture

CM (carboxy modified) Sepharose was obtained from Sigma Chemical Co. (St. Louis, Mo.) in an ethanol/$H_2O$ mixture. The solution was estimated at 50% solids based on total volume occupied by the solid and liquid portions on extended standing. This suspension was then mixed uniformly and diluted to 10% solids. 200 μl of this stock was removed and calculated at 0.12 meq/gram to be 0.012 meq of acid total. Stock of EDAC and N-hydryoxysuccinimide were prepared and 5.0 equivalents of each activating reagent were added to this suspension. For this preparation, 13.2 mg (in 1.32 ml) HOSuc and 11.25 mg EDAC (in 1.02 ml) were used and 8.0 mg total of the PTA intercalator. After incubation for 2–24 hours, the suspensions were then cleaned by repeated washing and gentle centrifugation steps until no more color was removed from the solid upon dilution. A

EXAMPLE 6

Protocol for DNA Capture by Intercalator Modified Solid Phase

1. Place 50 μl of activated microparticles in a 1.5 ml eppendorf.

2. Add 150 μl of PBS and 1–20 u of a 5.0 kb linearized plasmid end-labeled with $^{32}P$. Alternatively, added 1–50 μl of biological sample or another purified DNA.

3. Mix by rotation for one hour at ambient temperature.

4. Pellet the microparticles by centrifugation at 5,000 rpm for 5 minutes.

5. Wash one or two times with 200 μl of PBS.

6. Releas the DNA by adding 50 μ of 0.5M NaOH and mix for 15 minutes at ambient temperature.

7. Centrifuged and collected the supernatant, which contains released DNA.

The efficiency of DNA capture was measured using $^{32}P$ radiolabelled plasmid DNA in the above-described protocol. The results are found in FIG. 11 using the intercalator modified polystyrene microparticles prepared as per Example 4 and FIG. 12 and using the intercalator modified CM Sepharose beads prepared per Example 5. The data indicates that the DNA binding to the intercalator modified solid phase was specific and induced by the covalent attachment of intercalator V to the solid phase.

EXAMPLE 7

Relative Staining Intensities of Ethidium Homodimer and Phenanthridinium Triamine V (PTA) in a Flow Cytometric Study of Chicken Erythrocyte Nuclei (CEN)

Protocol: 50 μl of whole blood sample from two in-house donors and 3 μl of CEN suspension was added to 1.0 ml of pre-warmed at 40° C. WBC DIL without and with the NRBC dye at 1 μg/ml concentration, mixed, introduced to the FACScan™ and 20" readings were acquired. Chicken erythrocyte nuclei (CEN) were used to measure the brightness of the FL3 staining (mean FL3 of CEN). The whole blood samples used were about 4–5 hours old. The data for this experiment is shown in FIGS. 1–6.

EXAMPLE 8

Comparative Performance of Reduced Phenathidinium Triamine V Dye Concentrations Relative to Ethidium Homodimer The effect of a reduction in phenathidinium triamine V dye concentration (FIGS. 10A–F) relative to ethidium homodimer was demonstrated as follows:

Method: The experiment was designed to show the correlation between the dye concentration and the percent of FL2+ events in the UL quadrant on the FL1 versus FL2 dot plots. 50 ul of whole blood sample from each of two in-house donors was added to 1.0 ml of pre-warmed at 40° C. WBC DIL without and with the NRBC dye of varying concentration (0.25, 0.50, 0.75, and 1.0 ug/ml), mixed, introduced to the FACScan and 20" readings were acquired. Chicken erythrocyte nuclei (CEN) suspension was used to measure the brightness of the FL3 staining (mean FL3 of CEN). The whole blood samples used for this experiment were about 6 hours old.

It was observed that the CEN DNA is essentially indistinguishable from the background without the phenathidinium triamine V (FIG. 10B) and that the dye concentration can be reduced to 75% of that of ethidium homodimer (FIG. 5) and still maintain acceptable separation from the background (FIG. 10F). Such a reduction can lead to significantly reduced non-specific binding and substantial savings in dye usage.

EXAMPLE 9

Viability Dyes on the Coulter Elite Flow Cytometer

Cell Isolation Protocol: Each tube of ficol isolated cells were treated as follows: PBS with 0.1% NaAzide and 1.0% albumin (Sigma catalogue #1000-3) Ficol specific gravity 1.119 (Sigma Histopague catalogue #1119-1).

10 ml of whole blood (EDTA anticoagulant) was diluted with 10 ml of PBSW. Into 4, 15 ml conical bottom tubes, 5 ml of the diluted blood was layered over 5 ml of ficol. The tubes were spun for 30 minutes at 400×G. The interface layer which contains the lymphocytes, monocytes, granulocytes and platelets was aspirated and washed once in 5 ml PBS, by centrifuging tubes at 300×G for 6 minutes. The cell pellet was resuspended in PBS, cells counted, and adjusted to 8.5×10⁶ cells per ml.

Cell Staining Protocol:
Dye solutions:
PTA—Stock solution 10 ug/ml made by dissolving PTA in PBS with 0.1% NaAzide.
Propidium iodide (P.I.)—Stock solution 0.5 mg/ml made by dissolving P.I. in PBS with 0.1% NaAzide.
P.I. Staining:
In 12×75 mm tube, 117.6 ul of cells was mixed gently with 14.7 ul of P.I. stock dye solution. After 20 seconds, the tube was place on Elite flow cytometer and data collected.
Procedure from "Discrimination of Viable and Non-Viable Cells Using Popidium Iodide in Two Color Immunofluorescence" Cytometry by Sasaki et al., 1987, Vol. 8, pp. 413–420.
PTA Staining:
In 12×75 mm tube, 23.5 ul of cells was gently mixed with 76 ul of PTA stock dye solution. After 20 seconds, the tube was placed on Elite flow cytometer and data collected.
Trypan Blue Staining:
In 12×75 mm tube, 5 ul of working solution Trypan Blue and 5 ul of cells were gently mixed and cells counted in a mehacytometer using standard white light illumination. A minimum of 500 cells were counted within 3 minutes of staining.
Procedure from Selected Methods in Immunology by Mishell and Shiigi, 1980, pp. 16–17.

Flow cytometer protocol: Cells analyzed on the Elite flow cytometer (Coulter Electronics, Inc.).

Samples were excited with an argon laser at 488 nm and 15 mW of power. Data was gated on the basis of size and granularity to exclude red blood cells, platelets and debris. The linear dye fluorescence of the gated distribution was analyzed using unstained cells as a control. The percent positive events (dead cells) and the mean fluorescence of the dead cell distribution were recorded.

TABLE I

| Viability Dyes on the Coulter Elite | | |
| --- | --- | --- |
| Time Point | Sample | % Positive (Dead Cells) |
| 5 hr | P.I. | 2.5 |
| | PTA | 2.2 |
| | Trypan Blue | 1.4 |
| 27 hr | P.I. | 6.3 |
| | PTA | 7.7 |
| | Trypan Blue | 4.8 |
| 103 hr | P.I. | 26.8 |
| | PTA | 19.1 |
| | Trypan Blue | 10.2 |

While the present invention has been particularly shown with reference to specific materials and examples, it will be understood by those skilled in the art that changes in form and details can be made therein without departing from the spirit and scope of the invention.

We claim:

1. A method for detecting a target nucleic acid in a sample, said method comprising:
  (a) providing an amplification reaction mixture that comprises said sample, a DNA binding agent comprised of a compound comprised of aromatic and heteroaromatic segments functionalized with positively charged chains having the formula:

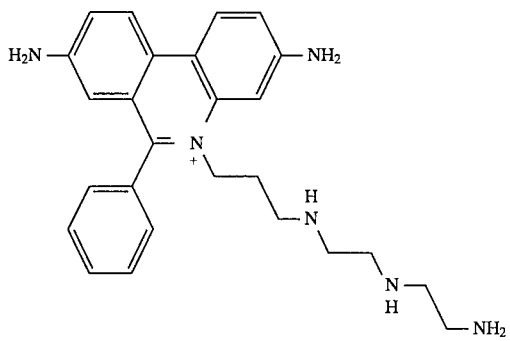

wherein said agent provides a detectable signal when bound to double stranded nucleic acid, which signal is distinguishable from the signal provided by said agent when it is unbound, and reagents for amplification;

(b) determining the amount of said signal produced by the mixture of step (a);

(c) treating said mixture under conditions for amplifying said target nucleic acid;

(d) determining the amount of said signal produced by said mixture of step (c); and (e) determining if amplification has occurred.

2. The method according to claim 1, wherein the DNA binding agent is further characterized as providing an amount of detectable signal when said agent is bound to double-stranded nucleic acids that is greater than the amount of said detectable signal produced when said agent is unbound.

3. The method of claim 2, wherein said DNA binding agent is an intercalating agent and is a fluorescent dye.

4. A method of separating a nucleic acid from a sample comprising: contacting a capture reagent with the sample wherein the capture agent comprises a compound comprised of aromatic and heteroaromatic segments functionalized with positively charged chains having the formula:

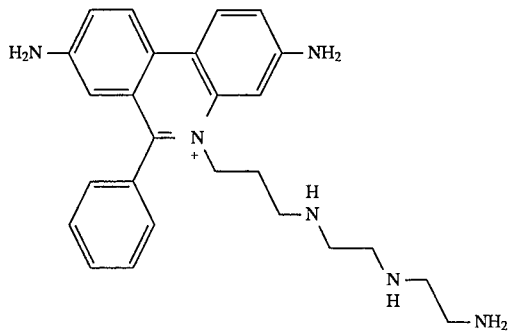

a solid support connected to the intercalating moiety by means of a linker molecule in a manner that allows the moiety to bind acid molecules in a sample, incubating the sample-capture regent mixture for a time sufficient to allow the capture reagent to bind with the nucleic acid in the sample to form capture reagent-nucleic acid complexes; and isolating the complexes from the sample.

5. A method according to claim 4, wherein the sample is treated so as to effect release of DNA.

6. A method according to claim 5, wherein the isolating step comprises centrifugation, filtration, or magnetic separation.

7. A method for determining one or more characteristics of cells using a fluorescence analysis comprising:

moving cells, substantially one at a time, in a liquid flow stream, said cells including at least one fluorescent marker comprising:

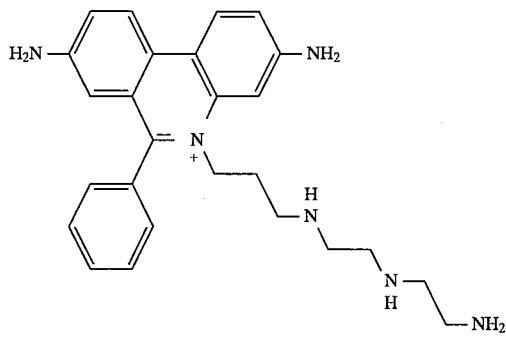

each marker having different emission spectra to permit detection thereof without substantial electronic spectral overlap;

directing an incident light beam of a single wavelength at the cells inset flow stream to excite the fluorescent markers with the single wavelength of light such that different wavelengths of fluorescence are emitted from the cell concomitant to the fluorescent energy transfer;

spectrally separating with optical elements the different wavelengths of emitted fluorescence to simultaneously refine the emitted fluoresce to enable this separate detection of the different wavelengths;

simultaneously detecting one or more different fluorescent emissions associated with cells moving in the flow stream; and using said detected fluorescence to determine one or more characteristics of said cells.

* * * * *

UNITED STATES PATENT AND TRADEMARK OFFICE
CERTIFICATE OF CORRECTION

PATENT NO. : 5,582,984
DATED : December 10, 1996
INVENTOR(S) : Bieniarz, et al.

It is certified that error appears in the above-indentified patent and that said Letters Patent is hereby corrected as shown below:

In the Title, change "PHENANTHRIDIUM" to --PHENANTHRIDINIUM--.

In the Abstract, line 1, change "Phenanthridium" to --Phenanthridinium--.

Column 1, line 1, change "PHENANTHRIDIUM" to --PHENANTHRIDINIUM--.

Column 8, line 20, change "phenathridinium" to --phenanthridinium--.

Column 8, lines 23-24, change "phenathridinium" to --phenanthridinium--.

Column 10, line 53, change "phenathridinium" to --phenanthridinium--.

Column 13, line 64, change "phenathridinium" to --phenanthridinium--.

Column 14, line 3-4, change "phenathridinium" to --phenanthridinium--.

Column 14, line 7, change "phenathridinium" to --phenanthridinium--.

Column 15, line 38-39, change "phenathridinium" to --phenanthridinium--.

UNITED STATES PATENT AND TRADEMARK OFFICE
CERTIFICATE OF CORRECTION

PATENT NO. : 5,582,984
DATED : December 10, 1996
INVENTOR(S) : Bieniarz, et al.

It is certified that error appears in the above-indentified patent and that said Letters Patent is hereby corrected as shown below:

Column 15, line 49-50, change "phenathridinium" to --phenanthridinium--.

Column 17, line 22-23, change "phenanthidinium" to --phenanthridinium--.

Column 18, line 14, change "phenathridium" to --phenanthridinium--.

Column 19, line 21, change "Phenathridium" to --Phenanthridinium--.

Column 23, line 30, change "Phenathidinium" to --Phenanthridinium--.

Column 23, line 33, change "phenathidinium" to --phenanthridinium--.

Column 23, line 49-50, change "phenathidinium" to --phenanthridinium--.

Signed and Sealed this

Ninth Day of September, 1997

Attest:

BRUCE LEHMAN

Attesting Officer

Commissioner of Patents and Trademarks